US009133225B2

(12) United States Patent
Lippard et al.

(10) Patent No.: US 9,133,225 B2
(45) Date of Patent: Sep. 15, 2015

(54) DUAL TARGETING ANTICANCER AGENTS

(71) Applicant: Massachusetts Institute of Technology, Cambridge, MA (US)

(72) Inventors: Stephen J. Lippard, Cambridge, MA (US); Ying Song, Cambridge, MA (US); Kogularamanan Suntharalingam, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/209,089

(22) Filed: Mar. 13, 2014

(65) Prior Publication Data

US 2014/0274988 A1  Sep. 18, 2014

Related U.S. Application Data

(60) Provisional application No. 61/779,832, filed on Mar. 13, 2013.

(51) Int. Cl.
*C07F 15/00* (2006.01)
*A61K 31/555* (2006.01)

(52) U.S. Cl.
CPC ........... *C07F 15/0093* (2013.01); *A61K 31/555* (2013.01)

(58) Field of Classification Search
USPC .......................................... 514/186; 549/211
See application file for complete search history.

(56) References Cited

U.S. PATENT DOCUMENTS

| | | | |
|---|---|---|---|
| 4,843,161 A | 6/1989 | Lippard et al. | |
| 5,244,919 A | 9/1993 | Abrams et al. | |
| 6,806,289 B1 | 10/2004 | Lippard et al. | |
| 7,138,520 B2 | 11/2006 | Lippard et al. | |
| 7,232,919 B2 | 6/2007 | Lal | |
| 8,729,286 B2 | 5/2014 | Lippard et al. | |
| 2004/0235712 A1 | 11/2004 | Lippard et al. | |
| 2005/0090478 A1 | 4/2005 | Barenholz et al. | |
| 2007/0082882 A1 | 4/2007 | Farrell | |
| 2007/0104654 A1 | 5/2007 | Hsieh et al. | |
| 2007/0154398 A1 | 7/2007 | Wang et al. | |
| 2010/0330197 A1 | 12/2010 | Higashiguchi et al. | |
| 2011/0257261 A1 | 10/2011 | Lippard et al. | |
| 2011/0300219 A1 | 12/2011 | Lippard et al. | |
| 2013/0029959 A1 | 1/2013 | Lippard et al. | |
| 2013/0303606 A1 | 11/2013 | Lippard et al. | |
| 2014/0343139 A1 | 11/2014 | Lippard et al. | |

FOREIGN PATENT DOCUMENTS

| | | |
|---|---|---|
| DE | 19623746 A1 | 12/1997 |
| EP | 0 199 524 B1 | 2/1992 |
| EP | 0 679 656 A1 | 11/1995 |
| WO | WO 2005/092298 A1 | 10/2005 |
| WO | WO 2006/108276 A1 | 10/2006 |
| WO | WO 2007/021852 A2 | 2/2007 |
| WO | WO 2007/124314 A2 | 11/2007 |
| WO | WO 2007/133807 A2 | 11/2007 |
| WO | WO 2008/121949 A1 | 10/2008 |
| WO | WO 2009/032172 A2 | 3/2009 |
| WO | WO 2010/047765 A2 | 4/2010 |
| WO | WO 2010/150036 A1 | 12/2010 |
| WO | WO 2012/177935 A1 | 12/2012 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286,531-537.*
Mi et al., Vitamin E TPGS prodrug micelles for hydrophilic drug delivery with neuroprotective effects, 2012, International Journal of Pharmaceutics, 438, 98-106.*
Abramkin et al., Solid-phase synthesis of oxaliplatin-TAT peptide bioconjugates. Dalton Trans. Mar. 14, 2012;41(10):3001-5. doi: 10.1039/c2dt12024k. Epub Jan. 27, 2012.
Al-Allaf et al., Platinum(II) and palladium(II) complexes analogous to oxaliplatin with different cyclohexyldicarboxylate isomeric anions and their in vitro antitumour activity. Structural elucidation of [Pt(C2O4)(cis-dach)]. Transition Metal Chemistry. 2003;28: 717-21.
Anderson et al., Alpha-TEA plus cisplatin reduces human cisplatin-resistant ovarian cancer cell tumor burden and metastasis. Exp Biol Med (Maywood). Dec. 2004;229(11):1169-76.
Ang et al., Transcription inhibition by platinum-DNA cross-links in live mammalian cells. J Am Chem Soc. Jun. 2, 2010;132(21):7429-35. doi: 10.1021/ja101495v.

(Continued)

*Primary Examiner* — Kristin Vajda
(74) *Attorney, Agent, or Firm* — Wolf, Greenfield & Sacks, P.C.

(57) ABSTRACT

Methods, compounds, and compositions for treating a proliferative disorder or other physiological conditions via a dual targeting anticancer therapy are provided. In some embodiments, a dual targeting anticancer therapy may utilize a composition comprising a platinum agent. The platinum agent may comprise a precursor to a therapeutically active platinum compound and at least one precursor to a vitamin E agent. The vitamin E agent may target cancer cells via a different mechanism of action than the therapeutically active platinum compound resulting in a dual targeting anticancer agent. The method of treatment may involve administering to a patient the dual targeting anticancer agent. Following administration, a therapeutically active platinum compound and a vitamin E agent may form at the physiologically relevant site. In some embodiments, administering a platinum agent comprising precursors of therapeutically active agents may be more effective than individually or simultaneously administering separate molecules of those therapeutically active agents.

18 Claims, 6 Drawing Sheets

(56) References Cited

OTHER PUBLICATIONS

Barragan et al., Solid-phase synthesis and DNA binding studies of dichloroplatinum(ii) conjugates of dicarba analogues of octreotide as new anticancer drugs. Chem Commun (Camb). Aug. 21, 2009;(31):4705-7. doi: 10.1039/b909698a. Epub Jun. 22, 2009.

Barragan et al., Somatostatin subtype-2 receptor-targeted metal-based anticancer complexes. Bioconjug Chem. Sep. 19, 2012;23(9):1838-55. Epub Aug. 20, 2012.

Bauer et al., Monofunctional platinum amine complexes destabilize DNA significantly. Eur J Biochem. Sep. 1, 1998;256(2):253-60.

Borrelli et al., A molecular carrier to transport and deliver cisplatin into endometrial cancer cells. Chem Biol Drug Des. Jul. 2012;80(1):9-16. doi: 10.1111/j.1747-0285.2012.01337.x. Epub Apr. 27, 2012.

Cohen et al., Binding of cis- and trans-dichlorodiammineplatinum(II) to DNA: evidence for unwinding and shortening of the double helix. Science. Mar. 9, 1979;203(4384):1014-6.

Comess et al., Replication inhibition and translesion synthesis on templates containing site-specifically placed cis-diamminedichloroplatinum(II) DNA adducts. Biochemistry. Apr. 28, 1992;31(16):3975-90.

Costello et al., Evidence for changes in RREB-1, ZIP3, and Zinc in the early development of pancreatic adenocarcinoma. J Gastrointest Cancer. Dec. 2012;43(4):570-8. doi: 10.1007/s12029-012-9378-1.

Cullen et al., Mitochondria as a critical target of the chemotheraputic agent cisplatin in head and neck cancer. J Bioenerg Biomembr. Feb. 2007;39(1):43-50.

Damian et al., Synthesis and DNA Interaction of Platinum Complex/Peptide Chimera as Potential Drug Candidates. Eur J Org Chem. Nov. 2010; 2010(32): 6161-70.

Deng et al., Crystallographic characterization of trans-bis(acetato)(1,1-cyclobutanedicarboxylato)ethylenediamineplatinum(IV) trihydrate. Inorganica Chimica Acta. Feb. 1, 1993;204(1):35-38.

De Pascali et al., First Examples of β-Diketonate Platinum(II) Complexes with Sulfoxide Ligands. Eur Journal of Inorg Chem. Feb. 2005; (4): 788-96.

De Pascali et al., Mutagenic Tests Confirm That New Acetylacetonate Pt(II) Complexes Induce Apoptosis in Cancer Cells Interacting with Nongenomic Biological Targets. Met Based Drugs. 2011;2011:763436. doi: 10.1155/2011/763436. Epub Apr. 10, 2011.

Desoize et al., Particular aspects of platinum compounds used at present in cancer treatment. Crit Rev Oncol Hematol. Jun. 2002;42(3):317-25.

Dhar et al., Current Status and Mechanism of Action of Platinum-Based Anticancer Drugs. Bioinorganic Medicinal Chemistry, Enzo Alessio, Ed. Wi-ley-VCH Verlag GmbH & Co. KgaA. Weinheim, Germany, Chapter 3. 2010:79-95.

Dhar et al., Mitaplatin, a potent fusion of cisplatin and the orphan drug dichloroacetate. Proc Natl Acad Sci U S A. Dec. 29, 2009;106(52):22199-204. doi: 10.1073/pnas.0912276106. Epub Dec. 10, 2009.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Dhar et al., Targeted single-wall carbon nanotube-mediated Pt(IV) prodrug delivery using folate as a homing device. J Am Chem Soc. Aug. 27, 2008;130(34):11467-76. doi: 10.1021/ja803036e. Epub Jul. 29, 2008.

Dodd et al., Peptide nucleic acid Pt(II) conjugates: a preliminary study of antisense effects in Xenopus laevis. Nucleosides Nucleotides Nucleic Acids. Apr. 2011;30(4):257-63. doi: 10.1080/15257770.2011.580290.

Dorwald, Side Reactions in Organic Synthesis: A Guide to Successful Design. Wiley VCH GmbH & Co. KGaA. 2005. pp. 1-15.

Feazell et al., Soluble single-walled carbon nanotubes as longboat delivery systems for platinum(IV) anticancer drug design. J Am Chem Soc. Jul. 11, 2007;129(27):8438-9. Epub Jun. 15, 2007.

Fink et al., In vitro and in vivo resistance to cisplatin in cells that have lost DNA mismatch repair. Cancer Res. May 15, 1997;57(10):1841-5.

Fink et al., The role of DNA mismatch repair in platinum drug resistance. Cancer Res. Nov. 1, 1996;56(21):4881-6.

Galanski et al., Update of the preclinical situation of anticancer platinum complexes: novel design strategies and innovative analytical approaches. Curr Med Chem. 2005;12(18):2075-94.

Gaviglio et al., Synthesis and in vitro cytotoxicity of cis,cis,trans-diamminedichloridodisuccinatoplatinum(IV)-peptide bioconjugates. Metallomics. Mar. 2012;4(3):260-6. doi: 10.1039/c2mt00171c. Epub Feb. 7, 2012.

Giandomenico et al., Carboxylation of Kinetically Inert Platinum(IV) Hydroxy Complexes. An Entr.acte.ee into Orally Active Platinum(IV) Antitumor Agents. Inorg Chem. Mar. 1995;34(5):1015-21. doi: 10.1021/ic00109a004.

Gill et al., Synthese, kinetics and mechanism of formation of polynuclear hydroxo-bridged complexes of (trans-1,2-diaminocyclohexane)platinum(II). J Am Chem Soc. 1982;104:4598-604.

Graf et al., Platinum(IV)-chlorotoxin (CTX) conjugates for targeting cancer cells. J Inorg Biochem. May 2012;110:58-63. doi: 10.1016/j.jinorgbio.2012.02.012. Epub Feb. 23, 2012.

Hall et al., Basis for design and development of platinum(IV) anticancer complexes. J Med Chem. Jul. 26, 2007;50(15):3403-11. Epub Jun. 28, 2007.

Hall et al. Platinum(IV) antitumour compounds: their bioinorganic chemistry. Coord Chem Rev. 2002; 232:49-67.

He et al., Steroid hormones induce HMG1 overexpression and sensitize breast cancer cells to cisplatin and carboplatin. Proc Natl Acad Sci U S A. May 23, 2000;97(11):5768-72.

Hoeschele et al., Synthesis and characterization of diastereomeric (substituted iminodiacetato)(1,2-diaminocyclohexane)platinum(II) complexess. Inorganic Chemistry. 1988;27:4106-13.

Hollis et al., Chemical and biological properties of a new series of cis-diammineplatinum(II) antitumor agents containing three nitrogen donors: cis-[Pt(NH3)2(N-donor)Cl]+. J Med Chem. Jan. 1989;32(1):128-36.

Hollis et al., Mechanistic studies of a novel class of trisubstituted platinum(II) antitumor agents. Cancer Res. Apr. 1, 1991;51(7):1866-75.

Hollis et al., Synthesis and Structures of Platinum(III) Complexes of α-Pyridone, [X(NH3)2Pt(C5H4NO)2Pt(NH3)2X](NO3)2*nH2O (X- = Cl-, NO2-, Br-). Inorg Chem. 1983;22:3637-44.

Howe-Grant et al., Aqueous Platinum (II) Chemistry; Binding to Biological Molecules. Metal Ions in Biological Systems. Sigel et al., eds. 1980;11:63-125.

Ivanov et al., Biological activity of platinum (II) complexes of the triamine type as a function of their composition and structure. Izv Akad Nauk Ser Biol. May-Jun. 1995;(3):281-90. English abstract found on p. 290.

Jamieson et al., Structure, Recognition, and Processing of Cisplatin-DNA Adducts. Chem Rev. 1999;99:2467-98.

Jin et al., Platinum(II) triammine antitumour complexes: structure—activity relationship with guanosine 5'-monophosphate (5'-GMP). Inorganica Chimica Acta. 2005;358:677-86.

Jung et al., RNA polymerase II blockage by cisplatin-damaged DNA. Stability and polyubiquitylation of stalled polymerase. J Biol Chem. Jan. 20, 2006;281(3):1361-70. Epub Nov. 7, 2005.

Kapp et al., Dinuclear alkylamine platinum(II) complexes of [1,2-bis(4-fluorophenyl)ethylenediamine]platinum(II): influence of endocytosis and copper and organic cation transport systems on cellular uptake. ChemMedChem. May 2006;1(5):560-4.

Kartalou et al., Mechanisms of resistance to cisplatin. Mutat Res. Jul. 1, 2001;478(1-2):23-43.

Kawai et al., Synthesis, structure and antitumor activity of a new water-soluble platinum complex, (1R,2R-cyclohexanediamine-N,N')[2-hydroxy-4-oxo-2-pentenoato(2-)-O2] platinum(II). Chem Pharm Bull (Tokyo). Feb. 1993;41(2):357-61.

(56) References Cited

OTHER PUBLICATIONS

Keck et al., Unwinding of supercoiled DNA by platinum-ethidium and related complexes. J Am Chem Soc. 1992;114:3386-90.
Kelland et al., The resurgence of platinum-based cancer chemotherapy. Nat Rev Cancer. Aug. 2007;7(8):573-84. Epub Jul. 12, 2007.
Kidani et al., Antitumor activity of 1,2-diaminocyclohexane—platinum complexes against sarcoma-180 ascites form. J Med Chem. Dec. 1978;21(12):1315-8.
Kostova, Platinum complexes as anticancer agents. Recent Pat Anticancer Drug Discov. Jan. 2006;1(1):1-22.
Lebwohl et al., Clinical development of platinum complexes in cancer therapy: an historical perspective and an update. Eur J Cancer. Sep. 1998;34(10):1522-34.
Lee et al., Transcription-coupled and DNA damage-dependent ubiquitination of RNA polymerase II in vitro. Proc Natl Acad Sci U S A. Apr. 2, 2002;99(7):4239-44. Epub Mar. 19, 2002.
Lempers et al., The new antitumor compound, cis-[Pt(NH3)2(4-methylpyridine)Cl]Cl, does not form N7,N7-d(GpG) chelates with DNA. An unexpected preference for platinum binding at the 5'G in d(GpG). J Inorg Biochem. Sep. 1990;40(1):23-35.
Lippard, Chemical synthesis: the art of chemistry. Nature. Apr. 11, 2002;416(6881):587.
Lovejoy et al., cis-Diammine(pyridine)chloroplatinum(II), a monofunctional platinum(II) antitumor agent: Uptake, structure, function, and prospects. Proc Natl Acad Sci U S A. Jul. 1, 2008;105(26):8902-7. doi: 10.1073/pnas.0803441105. Epub Jun. 25, 2008.
Lovejoy et al., Non-traditional platinum compounds for improved accumulation, oral bioavailability, and tumor targeting. Dalton Trans. Dec. 28, 2009;(48):10651-9. doi: 10.1039/b913896j. Epub Oct. 1, 2009.
Lovejoy et al., Spectrum of cellular responses to pyriplatin, a monofunctional cationic antineoplastic platinum(II) compound, in human cancer cells. Mol Cancer Ther. Sep. 2011;10(9):1709-19. doi: 10.1158/1535-7163.MCT-11-0250. Epub Jul. 12, 2011.
Malafa et al., Vitamin E succinate promotes breast cancer tumor dormancy J Surg Res. Sep. 2000;93(1):163-70.
Malafa et al., Vitamin E succinate suppresses prostate tumor growth by inducing apoptosis. Int J Cancer. May 15, 2006;118(10):2441-7.
Margiotta et al., Sterically hindered complexes of platinum(II) with planar heterocyclic nitrogen donors. A novel complex with 1-methylcytosine has a spectrum of activity different from cisplatin and is able of overcoming acquired cisplatin resistance. J Inorg Biochem. Nov. 2006;100(11):1849-57. Epub Aug. 3, 2006.
Martin et al., Do structurally similar molecules have similar biological activity? J Med Chem. Sep. 12, 2002;45(19):4350-8.
Misset et al., Oxaliplatin clinical activity: a review. Crit Rev Oncol Hematol. Aug. 2000;35(2):75-93.
Mukhopadhyay et al., Conjugated platinum(IV)-peptide complexes for targeting angiogenic tumor vasculature. Bioconjug Chem. Jan. 2008;19(1):39-49. Epub Sep. 11, 2007.
Muscella et al., [Pt(O,O'-acac)(gamma-acac)(DMS)], a new Pt compound exerting fast cytotoxicity in MCF-7 breast cancer cells via the mitochondrial apoptotic pathway. Br J Pharmacol. Jan. 2008;153(1):34-49. Epub Nov. 19, 2007.
Muscella et al., New platinum(II) complexes containing both an O,O'-chelated acetylacetonate ligand and a sulfur ligand in the platinum coordination sphere induce apoptosis in HeLa cervical carcinoma cells. Biochem Pharmacol. Jun. 30, 2007;74(1):28-40. Epub Mar. 31, 2007.
Muscella et al., Sublethal concentrations of the platinum(II) complex [Pt(O,O'-acac)(gamma-acac)(DMS)] alter the motility and induce anoikis in MCF-7 cells. Br J Pharmacol. Jul. 2010;160(6):1362-77. doi: 10.1111/j.1476-5381.2010.00782.x.
Ndinguri et al., Peptide targeting of platinum anti-cancer drugs. Bioconjug Chem. Oct. 21, 2009;20(10):1869-78. doi: 10.1021/bc900065r. Epub Sep. 23, 2009.

Neuzil et al., alpha-tocopheryl succinate-induced apoptosis in Jurkat T cells involves caspase-3 activation, and both lysosomal and mitochondrial destabilisation. FEBS Lett. Feb. 26, 1999;445(2-3):295-300.
Neuzil et al., Selective cancer cell killing by alpha-tocopheryl succinate. Br J Cancer. Jan. 5, 2001;84(1):87-9.
Neuzil, Vitamin E succinate and cancer treatment: a vitamin E prototype for selective antitumour activity. Br J Cancer. Nov. 17, 2003;89(10):1822-6.
Osol [Editor]. "Chapter 27: Structure-Activity Relationship and Drug Design". Remington's Pharmaceutical Sciences (Sixteenth Edition). Mack Publishing. 1980. pp. 420-435.
Page et al., Effect of the diaminocyclohexane carrier ligand on platinum adduct formation, repair, and lethality. Biochemistry. Jan. 30, 1990;29(4):1016-24.
Park et al., Phenanthriplatin, a monofunctional DNA-binding platinum anticancer drug candidate with unusual potency and cellular activity profile. Proc Natl Acad Sci U S A. Jul. 24, 2012;109(30):11987-92. doi: 10.1073/pnas.1207670109. Epub Jul. 6, 2012.
Peer et al., Nanocarriers as an emerging platform for cancer therapy. Nat Nanotechnol. Dec. 2007;2(12):751-60. doi: 10.1038/nnano.2007.387.
Pérez et al., Current status of the development of trans-platinum antitumor drugs. Crit Rev Oncol Hematol. Aug. 2000;35(2):109-20.
Pinto et al., Binding of the antitumor drug cis-diamminedichloroplatinum(II) (cisplatin) to DNA. Biochim Biophys Acta. 1985;780(3):167-80.
Portney et al., Nano-oncology: drug delivery, imaging, and sensing. Anal Bioanal Chem. Feb. 2006;384(3):620-30. Epub Jan. 27, 2006.
Quin et al., Vitamin E succinate decreases lung cancer tumor growth in mice. J Surg Res. Aug. 2005;127(2): 139-43.
Rabik et al., Molecular mechanisms of resistance and toxicity associated with platinating agents. Cancer Treat Rev. Feb. 2007;33(1):9-23. Epub Nov. 3, 2006.
Reardon et al., Efficient nucleotide excision repair of cisplatin, oxaliplatin, and Bis-aceto-ammine-dichloro-cyclohexylamine-platinum(IV) (JM216) platinum intrastrand DNA diadducts. Cancer Res. Aug. 15, 1999;59(16):3968-71.
Reardon et al., Purification and characterization of Escherichia coli and human nucleotide excision repair enzyme systems. Methods Enzymol. 2006;408:189-213.
Robillard et al. Solid-phase synthesis of peptide-platinum complexes using platinum-chelating building blocks derived from amino acids. New J Chem. 2005. 29: 220-5.
Robillard et al., Automated parallel solid-phase synthesis and anticancer screening of a library of peptide-tethered platinum(II) complexes. J Comb Chem. Nov.-Dec. 2003;5(6):821-5.
Robillard et al., The First Solid-Phase Synthesis of a Peptide-Tethered Platinum(II) Complex. Angew Chem Int Ed Engl. Sep. 1, 2000;39(17):3096-3099.
Robillard et al., The interaction of peptide-tethered platinum(II) complexes with DNA. J Inorg Biochem. Aug. 1, 2003;96(2-3):331-8.
Sakai et al., A New One-Dimensional Platinum System Consisting of Carboxylate-Bridged cis-Diammineplatinum Dimers1. JACS. 1998;120:11353-63.
Schwartz et al., Preparation and antitumor evaluation of water-soluble derivatives of dichloro(1,2-diaminocyclohexane)platinum(II). Cancer Treat Rep. Nov. 1977;61(8):1519-25.
Shiau et al., alpha-Tocopheryl succinate induces apoptosis in prostate cancer cells in part through inhibition of Bcl-xL/Bcl-2 function. J Biol Chem. Apr. 28, 2006;281(17):11819-25. Epub Mar. 6, 2006.
Siddik, Cisplatin: mode of cytotoxic action and molecular basis of resistance. Oncogene. Oct. 20, 2003;22(47):7265-79.
Silverman et al., 2.4-A crystal structure of the asymmetric platinum complex [Pt(ammine)(cyclohexylamine)]2+ bound to a dodecamer DNA duplex. J Biol Chem. Dec. 20, 2002;277(51):49743-9. Epub Oct. 10, 2002.
Spingler et al., 2.4 A crystal structure of an oxaliplatin 1,2-d(GpG) intrastrand cross-link in a DNA dodecamer duplex. Inorg Chem. Oct. 22, 2001;40(22):5596-602.

(56) References Cited

OTHER PUBLICATIONS

Sporn et al., Chemoprevention of cancer. Carcinogenesis. Mar. 2000;21(3):525-30.

Stephen et al., The structural characterisation and elucidation of the electronic structure of the mononuclear Pt(III) complex [Pt([9]aneS3)2]3+ ([9]aneS3 = 1,4,7-trithiacyclononane). Chem Commun (Camb). Nov. 30, 2008;(44):5707-9. doi: 10.1039/b811645h. Epub Sep. 30, 2008.

Suntharalingam et al., Conjugation of vitamin E analog α-TOS to Pt(IV) complexes for dual-targeting anticancer therapy. Chem Commun (Camb). Mar. 7, 2014;50(19):2465-8. doi: 10.1039/c3cc48740g. Epub Jan. 23, 2014.

Takahara et al., Crystal structure of the anticancer drug cisplatin bound to duplex DNA. J Am Chem Soc. 1996;118:12309-21.

Thoppil et al., Terpenoids as potential chemopreventive and therapeutic agents in liver cancer. World J Hepatol. Sep. 27, 2011;3(9):228-49. doi: 10.4254/wjh.v3.i9.228.

Todd et al., Inhibition of transcription by platinum antitumor compounds. Metallomics. 2009;1(4):280-91. doi: 10.1039/b907567d.

Trafton, MIT researchers see alternative to common colorectal cancer drug. News Office. Jun. 17, 2008. Last accessed Jun. 23, 2008. 2 pages.

Van Zutphen et al., Combinatorial discovery of new asymmetric cis platinum anticancer complexes is made possible with solid-phase synthetic methods. J Inorg Biochem. Oct. 2005;99(10):2032-8.

Van Zutphen et al., Extending solid-phase methods in inorganic synthesis: the first dinuclear platinum complex synthesised via the solid phase. Chem Commun (Camb). Mar. 7, 2003;(5):634-5.

Walker et al., Influence of the antioestrogen tamoxifen on normal breast tissue. Br J Cancer. Oct. 1991;64(4):764-8.

Wang et al., Cellular processing of platinum anticancer drugs. Nat Rev Drug Discov. Apr. 2005;4(4):307-20.

Wang et al., X-ray structure and mechanism of RNA polymerase II stalled at an antineoplastic monofunctional platinum-DNA adduct. Proc Natl Acad Sci U S A. May 25, 2010;107(21):9584-9. doi: 10.1073/pnas.1002565107. Epub May 6, 2010.

Weiss et al., New cisplatin analogues in development. A review. Drugs. Sep. 1993;46(3):360-77.

Whittaker et al., The interaction of DNA-targeted platinum phenanthridinium complexes with DNA. Nucleic Acids Res. Sep. 1, 1998;26(17):3933-9.

Wilson et al., Acetate-bridged platinum(III) complexes derived from cisplatin. Inorg Chem. Sep. 17, 2012;51(18):9852-64. doi: 10.1021/ic301289j. Epub Sep. 4, 2012.

Wilson et al., Synthesis, characterization, and cytotoxicity of platinum(IV) carbamate complexes. Inorg Chem. Apr. 4, 2011;50(7):3103-15. doi: 10.1021/ic2000816. Epub Mar. 1, 2011.

Wilson, New Constructs for Platinum Anticancer Prodrugs. Presentation. Oct. 19, 2011. 41 pages.

Wisnovsky et al., Targeting mitochondrial DNA with a platinum-based anticancer agent. Chem Biol. Nov. 21, 2013;20(11):1323-8. doi: 10.1016/j.chembiol.2013.08.010. Epub Oct. 31, 2013.

Wong et al., Current status of platinum-based antitumor drugs. Chem Rev. Sep. 8, 1999;99(9):2451-66.

Wong et al., Harnessing chemoselective imine ligation for tethering bioactive molecules to platinum(IV) prodrugs. Dalton Trans. May 28, 2012;41(20):6104-11. doi: 10.1039/c2dt30264k. Epub Mar. 16, 2012.

Yalçin, Studies on cis-DDP, [Pt(Dach)(MePhSO)Cl]+ and [PtNH3)2(N-Py)Cl]+ binding to fumarase. Drug Metabol Drug Interact. 1995;12(2):105-15.

Yonezawa et al., Cisplatin and oxaliplatin, but not carboplatin and nedaplatin, are substrates for human organic cation transporters (SLC22A1-3 and multidrug and toxin extrusion family). J. Pharmacol Exp Ther. Nov. 2006;319(2):879-86. Epub Aug. 16, 2006.

Zamble et al., Cisplatin and DNA repair in cancer chemotherapy. Trends Biochem Sci. Oct. 1995;20(10):435-9.

Zamble et al., Repair of cisplatin—DNA adducts by the mammalian excision nuclease. Biochemistry. Aug. 6, 1996;35(31):10004-13.

Zhang et al., Organic cation transporters are determinants of oxaliplatin cytotoxicity. Cancer Res. Sep. 1, 2006;66(17):8847-57.

Zhu et al., Monofunctional platinum-DNA adducts are strong inhibitors of transcription and substrates for nucleotide excision repair in live mammalian cells. Cancer Res. Feb. 1, 2012;72(3):790-800. doi: 10.1158/0008-5472.CAN-11-3151. Epub Dec. 16, 2011.

Zorbas-Seifried et al., Reversion of structure-activity relationships of antitumor platinum complexes by acetoxime but not hydroxylamine ligands. Mol Pharmacol. Jan. 2007;71(1):357-65.

International Search Report and Written Opinion for PCT/US2014/026064 mailed Nov. 28, 2014.

\* cited by examiner

DUAL TARGETING ANTICANCER AGENTS

RELATED APPLICATIONS

This application claims priority under 35 U.S.C. §119(e) to U.S. Provisional Patent Application, U.S. Ser. No. 61/779,832, filed Mar. 13, 2013, entitled "Vitamin E Analogs Conjugated Pt(IV) Complexes as Dual Targeting Anticancer Agents," which is incorporated herein by reference in its entirety.

STATEMENT REGARDING FEDERALLY SPONSORED RESEARCH OR DEVELOPMENT

This invention was made with government support under Grant No. 5-R37-CA034992, awarded by the NIH. The government has certain rights in this invention.

FIELD OF THE INVENTION

The present invention relates to compounds, compositions, kits, and methods for the treatment of proliferative diseases using a compound comprising at least a first component comprising a precursor of a therapeutically active platinum compound and a second component comprising a precursor of a vitamin E agent.

BACKGROUND OF THE INVENTION

Platinum drugs are widely used in cancer therapy, because they induce apoptosis by damaging nuclear DNA in cancer cells. Among the platinum drugs, cisplatin, carboplatin, and oxaliplatin have FDA approval and are clinically used in the United States and elsewhere. The use of platinum(II) drugs in the treatment of malignancies has been somewhat limited because of the side effects and resistance acquired by cancer cells. An alternative to platinum(II) drug candidates is the use of substitutionally more inert platinum(IV) compounds as prodrugs derived from clinically effective platinum(II) compounds. Substitutionally inert platinum(IV) complexes are less likely to be deactivated prior to reaching their destination target in the cancer cell. The activity of platinum(IV) complexes generally involves reduction with concomitant loss of the axial ligands, affording an active platinum(II) complex that readily binds to DNA. The axial ligands which are released from the platinum(IV) complex may comprise a therapeutically active agent with the same or different mechanism of action as the resulting platinum(II) drug. Single agents with dual targeting capabilities provide a powerful approach to treating cancer. Therefore, it would be beneficial to have methods, compounds, and compositions for treating cancer using a single platinum(IV) agent with dual targeting capabilities.

SUMMARY OF THE INVENTION

The present invention provides compounds, compositions, preparations, formulations, kits, and methods useful for treating subjects having proliferative diseases or at risk of developing cancer. More specifically, the present invention relates to compounds, compositions, kits, and methods for treatment of cancers using a compound comprising at least a first component comprising a precursor of a therapeutically active platinum compound and a second component comprising a precursor of a vitamin E agent. The subject matter of the present invention involves, in some cases, interrelated products, alternative solutions to a particular problem, and/or a plurality of different uses of one or more systems and/or articles.

In one aspect, compounds are provided. In one set of embodiments, a platinum(IV) compound comprises at least one vitamin E analog, wherein the vitamin E analog is associated with the platinum center.

In another set of embodiments, a compound has the formula:

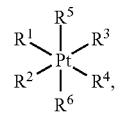

wherein $R^1$, $R^2$, $R^3$, and $R^4$ can be the same or different and each is a group comprising at least one of halogen, ammonia, $-N(R')_2$, $-OR'$, an aryl group, heteroaryl, a heterocycle including at least one nitrogen, or a leaving group, any being optionally substituted, or any two or three of $R^1$, $R^2$, $R^3$ and $R^4$ can be joined together to form a bidentate ligand or tridentate ligand, any being optionally substituted, each R' is independently hydrogen, alkyl, alkenyl, alkynyl, aryl, heteroaryl, or acyl, any being optionally substituted, or any two R' may be joined together to form a ring, and $R^5$ and $R^6$ can be the same or different, and at least one is a vitamin E agent, when dissociated from the platinum; or a pharmaceutically acceptable salt.

In one set of embodiments, a compound has the formula:

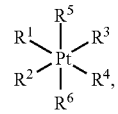

wherein $R^1$ and $R^2$ can be the same or different and each is a group comprising at least one of halogen, ammonia, $-N(R')_2$, $-OR'$, an aryl group, heteroaryl, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted, each R' is independently hydrogen, alkyl, alkenyl, alkynyl, aryl, heteroaryl, or acyl, any being optionally substituted, or any two R' may be joined together to form a ring, and $R^3$, $R^4$, $R^5$, and $R^6$ can be the same or different, and at least one is vitamin E agent, when dissociated from the platinum; or a pharmaceutically acceptable salt.

Figure 1A:
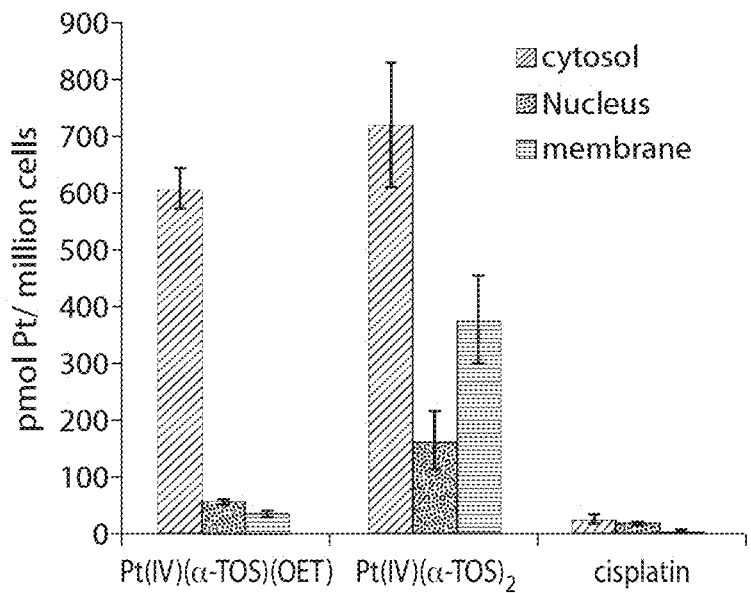
FIGS. 1A-B show (A) a plot of cellular uptake of Pt(IV)(α-TOS)$_2$, Pt(IV)(α-TOS)(OEt), and cisplatin in A549 cells and (B) a plot of platinum content in genomic DNA extracted from A549 cells treated with cisplatin, mixtures of α-TOS and cisplatin, Pt(IV)(α-TOS)$_2$, Pt(IV)(α-TOS)(OEt), and Pt(IV)(OAc)$_2$.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Methods, compounds, and compositions for treating a proliferative disorder (e.g., cancer) or other physiological conditions via a dual targeting anticancer therapy are provided. In some embodiments, a dual targeting anticancer therapy may utilize a composition comprising a platinum agent. The platinum agent may comprise a precursor to a therapeutically active platinum compound and at least one precursor to a vitamin E agent. The vitamin E agent may target cancer cells via a different mechanism of action than the therapeutically active platinum compound resulting in a dual targeting anticancer agent. The method of treatment may involve administering to a patient the dual targeting anticancer agent. Following administration, a therapeutically active platinum compound and a vitamin E agent may form at the physiologically relevant site. In some embodiments, administering a platinum agent comprising precursors of therapeutically active agents may be more effective than individually or simultaneously administering separate molecules of those therapeutically active agents (e.g., vitamin E agent, therapeutically active platinum compound).

In some embodiments, the methods, compounds, and compositions, described herein, may be used to overcome certain limitations of traditional platinum(II) drugs. Despite the success of certain platinum(II) drugs, side effects, and cellular resistance have somewhat limited their utility. Platinum(IV) drugs have emerged as an alternative to some platinum(II) drugs. The platinum(IV) metal centers are more inert than platinum(II) and are generally activated by reduction (e.g., in vivo, within a cell), which results in the generation of an active platinum(II) compound (or precursor of an active platinum (II) compound) and concomitant release of the axial ligands. The efficacy and pharmacokinetics of platinum(IV) drugs can be influenced by the axial ligands. Thus, certain conventional platinum(IV) drugs have selected axial ligands that minimally influence the properties of the resulting platinum(II) compound and/or have independent therapeutic activity. However, axial ligands are needed that are therapeutically active and act synergistically with the platinum (II) compound, such that the platinum(IV) drug has enhanced properties (e.g., cellular uptake, cancer cell cytotoxicity, cancer cell selectivity) compared to the therapeutically active platinum (II) compound, the therapeutically active axial ligand(s), and/or the mixture of separate molecules of the therapeutically active platinum (II) compound and axial ligand(s). Accordingly, better methods, compounds, and compositions are needed.

It has been discovered, within the context of certain embodiments of the present invention, that platinum(IV) agents comprising a precursor to a therapeutically active platinum compound and a precursor to a vitamin E agent have enhanced cellular uptake, cancer cell cytotoxicity, and cancer cell selectivity, amongst other properties, compared to the therapeutically active platinum compound alone, the vitamin E agent alone, and/or the mixture of separate molecules of the therapeutically active platinum compound and vitamin E agent. Without being bound by theory, it is believed that the enhanced properties are due at least to the lipophilicity of the vitamin E agent precursor, the comparable IC$_{50}$ between the therapeutically active platinum compound and the vitamin E agent, and the differing mechanism of actions of the therapeutically active platinum compound and the vitamin E agent.

A "vitamin E agent," as used herein, refers to members of the vitamin E family (e.g., alpha-tocopherol, beta-tocopherol, gamma-tocopherol, delta-tocopherol, alpha-tocotrienol, beta-tocotrienol, gamma-tocotrienol, delta-tocotrienol) and vitamin E analogs (e.g., alpha-tocopheryl succinate, alpha-tocopheryl acetate, alpha-tocopheryl nicotinate, alpha-tocopheryl oxyacetic acid). In some embodiments, a vitamin E analog may have similar or substantially the same activity as a vitamin E compound. In some embodiments a vitamin E agent may have the structure:

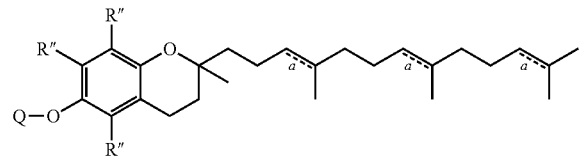

wherein each $\overline{\overline{a}}$ is independently a single or double bond; each R" is independently hydrogen or a methyl; and Q is hydrogen, optionally substituted alkyl, is optionally substituted alkylene, optionally substituted heteroalkyl, optionally substituted heteroalkylene, optionally substituted alkenyl, optionally substituted alkenylene, optionally substituted heteroalkenyl, optionally substituted heteroalkenylene, optionally substituted cycloheteroalkyl, optionally substituted cycloheteroalkylene, optionally substituted cycloheteroalkenyl, optionally substituted alkynyl, optionally substituted alkynylene, optionally substituted heteroalkynyl, optionally substituted heteroalkynylene, optionally substituted aryl, optionally substituted arylene, optionally substituted heteroaryl, optionally substituted heteroarylene, optionally substituted acyl, or optionally substituted phosphono group. It should be understood that the Q group may be monovalent or divalent. For example, a divalent Q group may be used to attach the vitamin E agent to the platinum metal or tether, forming the precursor to the vitamin E agent.

In some embodiments, certain members of the vitamin E family have the structure:

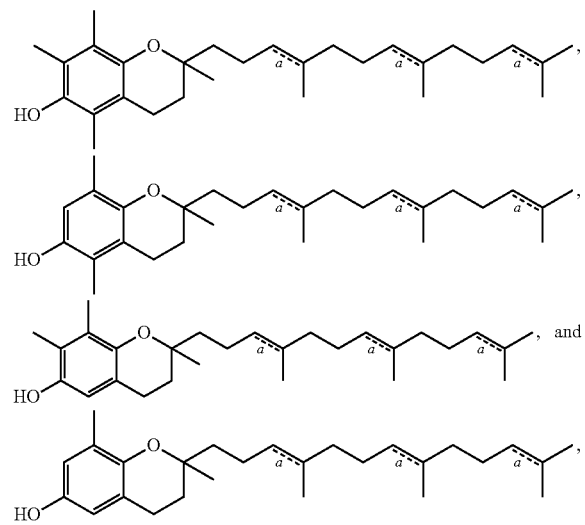

wherein each $\overline{\overline{a}}$ is independently a single or a double bond. In some embodiments, every $\overline{\overline{a}}$ is a single or every $\overline{\overline{a}}$ is a double bond. In certain embodiments, a vitamin E agent may be formed by functionalizing the hydroxyl moiety of the vitamin E agent with an analog moiety, e.g., Q. For example, vitamin E analogs may have the structure:

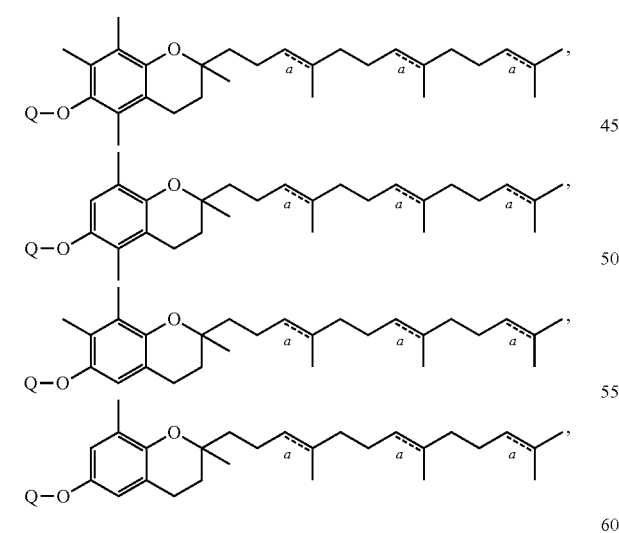

wherein each $\overline{\overline{a}}$ is independently a single or a double bond; and Q is optionally substituted alkyl, is optionally substituted alkylene, optionally substituted heteroalkyl, optionally substituted heteroalkylene, optionally substituted alkenyl, optionally substituted alkenylene, optionally substituted heteroalkenyl, optionally substituted heteroalkenylene, optionally substituted cycloheteroalkyl, optionally substituted cycloheteroalkylene, optionally substituted cycloheteroalkenyl, optionally substituted alkynyl, optionally substituted alkynylene, optionally substituted heteroalkynyl, optionally substituted heteroalkynylene, optionally substituted aryl, optionally substituted arylene, optionally substituted heteroaryl, optionally substituted heteroarylene, optionally substituted acyl, or optionally substituted phosphono group. In some embodiments, every $\overline{\overline{a}}$ is a single or every $\overline{\overline{a}}$ is a double bond. In some embodiments, Q may be an optionally substituted arylene, optionally substituted alkenyl or an optionally substituted acyl. In certain embodiments, Q may include one or more ester, amide, amine, ether, urea, carbamate, carbonate, or anhydride moiety. For instance, Q may have the structure:

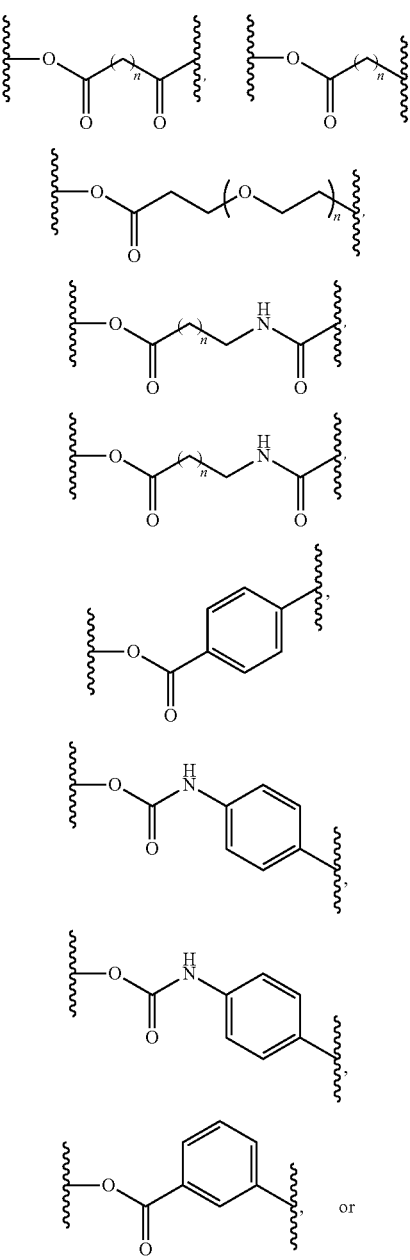

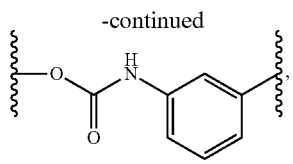

wherein n is 1, 2, 3, 4, 5, or 6. Those of ordinary skill in the art would understand the left to represent the connection (e.g., bond) to the platinum agent or tether and the right to represent the connection (e.g., bond) to the oxygen functional group in the vitamin E molecule. Those of ordinary skill of the art would be knowledgeable of the vitamin E family as well as vitamin E analogs.

"Precursor," as used herein, means a composition which, after undergoing loss and/or gain of a ligand, functional group, or the like, and/or undergoing a reaction (e.g., chemical reaction of a functional group), dissociation from a compound, agent, mixture, etc., is a therapeutically active agent effective at treating a subject in need of treatment for cancer (a subject at risk of, or currently or previously afflicted with cancer). In some embodiment, a precursor of a vitamin E agent may be formed by directly associating the vitamin E agent with a platinum center or associating the vitamin E agent to the platinum center via a tether. It should be understood, however, that in some embodiments, a precursor to a therapeutically active agent (e.g., precursor to a therapeutically active platinum compound) may form a second generation precursor to a therapeutically active agent. The second generation precursor may undergo transformation to form the therapeutically active agent, or, in some cases, a third generation precursor. In some embodiments, the precursor (or second generation precursor) to a therapeutically active agent may diminished or substantially no therapeutic activity relative to the therapeutically active agent.

In some embodiments, a compound comprising a precursor to a therapeutically active platinum compound and a precursor to a vitamin E agent has a structure according to Formula (I):

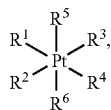

wherein:

$R^1$, $R^2$, $R^3$, and $R^4$ can be the same or different and each is a group comprising at least one of halogen, ammonia, —N(R')$_2$, —OR', an aryl group, heteroaryl, a heterocycle including at least one nitrogen, or a leaving group, any being optionally substituted, or any two or three of $R^1$, $R^2$, $R^3$ and $R^4$ can be joined together to form a bidentate ligand or tridentate ligand, any being optionally substituted, each R' is independently hydrogen, alkyl, alkenyl, alkynyl, aryl, heteroaryl, or acyl, any being optionally substituted, or any two R' may be joined together to form a ring, and $R^5$ and $R^6$ can be the same or different, and at least one is a vitamin E agent, when dissociated from the platinum; or a pharmaceutically acceptable salt.

In some embodiments, a compound comprising a precursor to a therapeutically active platinum compound and a precursor to a vitamin E agent has a structure according to Formula (II):

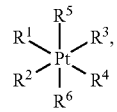

wherein:

$R^1$ and $R^2$ can be the same or different and each is a group comprising at least one of halogen, ammonia, —N(R')$_2$, —OR', an aryl group, heteroaryl, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted, each R' is independently hydrogen, alkyl, alkenyl, alkynyl, aryl, heteroaryl, or acyl, any being optionally substituted, or any two R' may be joined together to form a ring, and $R^3$, $R^4$, $R^5$, and $R^6$ can be the same or different, and at least one is vitamin E agent, when dissociated from the platinum; or a pharmaceutically acceptable salt.

Compounds, as described herein, (e.g., of Formula I and II) may have enhanced cellular uptake, cancer cell cytotoxicity, and cancer cell selectivity, amongst other properties, compared to the therapeutically active platinum compound alone, the vitamin E agent alone, and/or the mixture of separate molecules of the therapeutically active platinum compound and vitamin E agent. In some embodiments, the compounds, described herein, may exhibit greater cellular uptake than the therapeutically active platinum compound alone. It is believed that the relatively high lipophilicity of the vitamin E agent or precursor thereof may facilitate uptake of the platinum agent, such that cellular uptake of the platinum agent is greater than the cellular uptake of the corresponding therapeutically active platinum compound under essentially identical conditions. For instance, the platinum agent may have a 2-fold, 5-fold, 10-fold, 50-fold, 100-fold, 200-fold, 500-fold, or 1000-fold greater uptake than the therapeutically active platinum compound alone.

In some embodiments, the compounds comprising a precursor to a therapeutically active platinum compound and a precursor to a vitamin E agent may have enhanced cancer cell toxicity. For instance, in some embodiments, the IC$_{50}$ value of a compound of the present invention comprising a precursor of a therapeutically active platinum compound and a precursor of a vitamin E agent may be at least about 1%, at least about 2%, at least about 5%, at least about 10%, at least about 15%, at least about 20%, at least about 30%, at least about 40%, at least about 50%, at least about 60%, at least about 70%, at least about 100%, or more, greater than the IC$_{50}$ value of the therapeutically active platinum compound alone, the vitamin E agent alone, and/or the mixture of separate molecules of the therapeutically active platinum compound and the vitamin E agent, when administered in a substantially similar manner.

Without being bound by theory, it is believed that certain vitamin E agents induce apoptosis by disrupting mitochondrial function and therapeutically active platinum compounds induce apoptosis by damaging nuclear DNA, thereby imparting dual targeting capabilities to the platinum agent. Moreover, in some embodiments, the vitamin E agent and the therapeutically active platinum compound may have a similar IC$_{50}$, such that the effective dose of each therapeutically active agent (e.g., platinum (II) compound, vitamin E agent) can be achieved using the platinum agent.

In some embodiments, the compounds comprising a precursor to a therapeutically active platinum compound and a precursor to a vitamin E agent may exhibit selectivity toward cancer cells. That is, the compounds, described herein, may have deleterious effects on the cancer cells (e.g., causing death of the cells) and/or affect cancer cells to a higher degree (e.g., ten-fold, 50-fold, 100-fold, 200-fold, 500-fold, 1000-fold) than non-cancer cells. For example, exposure of a plurality of cancer cells and a plurality of non-cancer cells to the platinum agent may substantially affect the plurality of cancer cells (e.g., cause the cancer cells to die or leads to the cell death) and may not substantially affect the non-cancer cells (e.g., may not cause the non-cancer cells to die or may not lead to cell death). In some cases, a platinum agent may be determined to substantially affect cancer cells and have no substantial effect on non-cancer cells (e.g., the agent is substantially inactive towards non-cancer cells) by determining the ratio of cancer cells which are affected (e.g., resulting in cell death by the agent) to non-cancer cells which are affected, following exposure to the compounds, described herein.

In some embodiments, the ratio of cancer cells (e.g., ovarian cancer cells) to non-cancer cells which are affected (e.g., cell death) upon exposure to the compounds, described herein, at least about 2:1, is at least about 5:1, at least about 10:1, at least about 100:1, at least about 200:1, at least about 500:1, at least about 1000:1, at least about 5000:1, at least about 10,000:1, at least about 100,000:1, or greater. Those of ordinary skill in the art would be aware of methods and technologies for determining the ratio of cancer cells to non-cancer cells affected by the agent, as well as the number of cells which undergo cell death upon exposure to the agent. Other parameters may also be determined when determining whether an agent affects a cancer cell and/or a non-cancer cell, for example, tumor size, membrane potential of a cell, or presence or absence of a compound in parts of the cell (e.g., cytochrome c, apoptosis inducing factor, etc.).

In some embodiments, the compounds comprising a precursor to a therapeutically active platinum compound and a precursor to a vitamin E agent may have deleterious effects (e.g., causing death of the cells) and/or affect cancer cells that are resistant to the therapeutically active platinum compound to a higher degree (e.g., two-fold, five-fold, ten-fold, 50-fold, 100-fold, 200-fold, 500-fold, 1000-fold) than the therapeutically active platinum compound alone and/or the mixture of separate molecules of the therapeutically active platinum compound and the vitamin E agent. For example, compounds of Formula I and II may have enhance cytotoxicity against cancers (e.g., ovarian cancer, lung cancer, breast cancer, cervical cancer, prostate cancer, colon cancer) that are resistant to the therapeutically active platinum compound (e.g., platinum(II) compound, cisplatin) that dissociates from the compounds of Formula I and II.

It is to be understood that the specific compounds disclosed or exemplified herein are for purposes of illustration only, and other compounds can be used so long as they meet the requirements of the claimed invention. Those of ordinary skill in the art of chemical therapeutics can readily select first and second components, as described functionally herein, bound to each other in a way such that they can be delivered together to a treatment site, and partially or fully dissociate from each other to form a first therapeutically active agent (or second generation precursor) and a second therapeutically active agent (or second generation precursor), the second therapeutically active agent being a vitamin E agent.

In some embodiments, the present invention is directed towards compounds comprising at least a first component comprising a precursor of a therapeutically active platinum compound and a second component comprising a precursor of a vitamin E agent. In some embodiments, upon uptake of the composition into a cell, the first component and the second component dissociate from each other to form a platinum (II) therapeutically active agent or a second generation precursor to a platinum(II) therapeutically active agent and a vitamin E agent or a second generation precursor to a vitamin E agent.

The precursor to the vitamin E agent can be bound to the precursor to the first therapeutically active (e.g., platinum) agent in any of a number of ways including covalent bonding, ionic bonding, coordinative coupling, or the like. Typically, the vitamin E agent is covalently bound to the first therapeutically active agent. In certain embodiments, release of the vitamin E agent from the platinum center of the precursor to the therapeutically active platinum compound may be precipitated by a redox change of the platinum center. For example, the precursor to the therapeutically active platinum compound may comprise a platinum(IV) center which may be reduced to a platinum(II) center, as described herein. In certain instances, the redox change may cause the vitamin E agent to be released from the platinum center, whereas in other instances, the redox change could make it more likely that the vitamin E agent is subsequently released from the platinum. For example, a redox change of platinum may directly cause the vitamin E agent to dissociate from the platinum center immediately. An example of such an instance is a redox change that causes a change in coordination geometry for the platinum center that reduces the number of ligands, thereby causing the vitamin E agent to dissociate and thus be released. Alternatively, such a redox change may increase the likelihood that the vitamin E agent disassociates over time or is displaced by another ligand. For example, a redox change could make substitution at the platinum center more likely whereas before the redox change substitution was not as likely. In addition and without limitation, for all of the subject coordination complexes, it may be the case that a covalently attached precursor to a vitamin E agent is released over time after administration without any redox change at the metal center, notwithstanding whether a redox changes causes or increases the likelihood of release of the precursor to the vitamin E agent.

Figure 8:
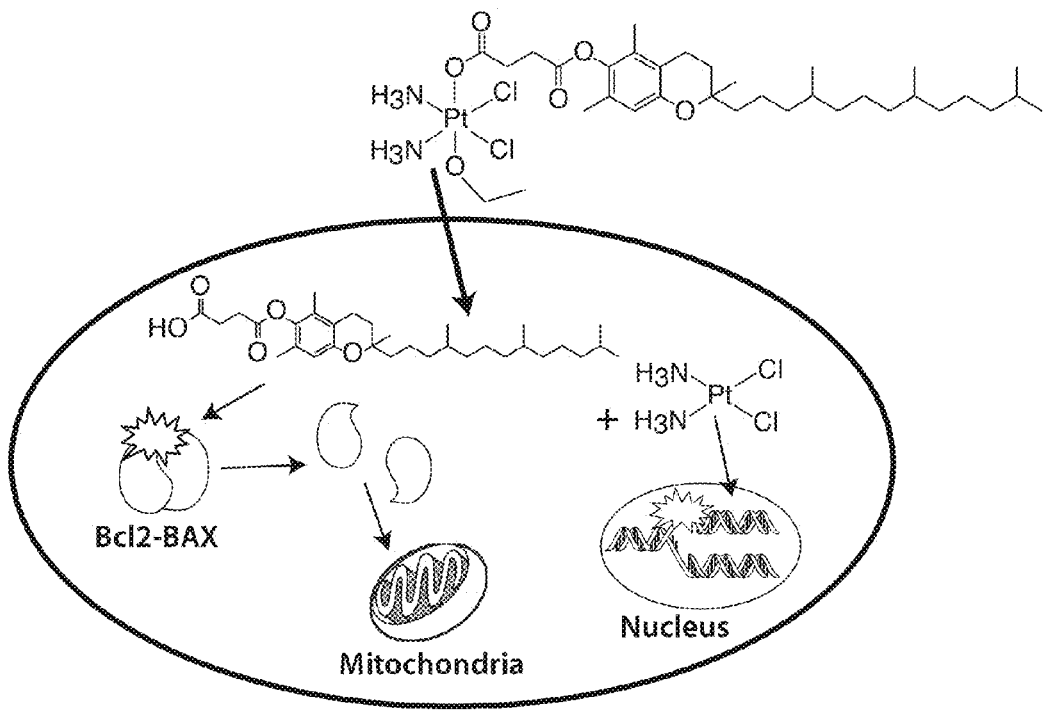
FIG. 8 shows a scheme of cellular uptake and reduction of a platinum agent.

The platinum(IV) composition may be more likely to undergo a redox change following uptake into a cell. That is, the reducing environment of a cell may lead to reduction of the platinum(IV) precursor to a platinum(II) therapeutically active agent as shown in FIG. 8. FIG. 8 shows a schematic of a platinum agent, as described herein, being taken up by a cell and reduced to form a vitamin E analog and cisplatin. As illustrated in FIG. 8, the vitamin E analog targets the mitochondria and cisplatin For example, a platinum(IV) agent may not be reduced to form a therapeutically active platinum (II) composition prior to uptake or diffusion into a cell. That is, the reducing environment within cells may facilitate or enhance a redox change at the platinum center, precipitating release of the precursor to the vitamin E agent. By this mechanism, for certain subject coordination complexes, release of a covalently attached therapeutically active agent precursor can occur (or be more likely to occur) in the cell upon reduction of the metal ion to which the therapeutically active agent precursor is covalently attached. By this means, the platinum(II) therapeutically active agent and the vitamin E agent may be generated in the same cell concomitantly. In some embodiments, the composition may be substantially therapeutically inactive prior to uptake into a cell (e.g., the composition has substantially no therapeutic activity prior to uptake into a cell, i.e., prior to reduction within the cell).

In one aspect, the present invention relates to methods for treating a patient, such as a patient indicated for treatment for a proliferative disease (e.g., cancer). According to the first set of embodiments, a method comprises administering to a patient a compound comprising at least a first component comprising a precursor of a therapeutically active platinum compound and a second component comprising a precursor of a vitamin E agent. In some embodiments, upon uptake of the composition into a cell, the first component and the second component dissociate from each other and form a therapeutically active platinum compound (or a second generation precursor to a therapeutically active platinum compound) and a vitamin E agent (or a second generation precursor to a vitamin E agent). In some embodiments, a first component of a compound comprises a platinum(IV) agent which is a precursor to a therapeutically active platinum compound (or a second generation precursor to therapeutically active platinum compound), while a second component comprises a precursor to a vitamin E agent (or a second generation precursor to a vitamin E agent). In certain embodiments, the proliferative disorder is lung cancer, cervical cancer, prostate cancer, colon cancer, breast cancer, or ovarian cancer.

In some aspects, the present inventions relates to compounds. According to a first set of embodiments, a compound having the formula,

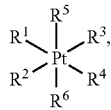

wherein, $R^1$, $R^2$, $R^3$, and $R^4$ can be the same or different and each is a group comprising at least one of halogen, ammonia, —N(R')$_2$, —OR', an aryl group, heteroaryl, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted; each R' is independently hydrogen, alkyl, alkenyl, alkynyl, aryl, heteroaryl, or acyl, any being optionally substituted, or any two R' may be joined together to form a ring; and $R^5$ and $R^6$ can be the same or different and at least one is a vitamin E agent, when dissociated from the platinum. The compound may also comprise a pharmaceutically acceptable salt.

In some embodiments, at least two of $R^1$, $R^2$, $R^3$, $R^4$, $R^5$ and $R^6$ are selected such that, upon exposure to a cellular or reducing environment, a therapeutically active platinum compound forms or a second generation precursor to a therapeutically active platinum compound forms. For example, $R^1$ and $R^2$ may be essential groups for the formation of a therapeutically active platinum compound (e.g., groups which are required for a platinum compound to be therapeutically active compound, wherein $R^3$-$R^6$ may be any variety of ligands and/or optionally absent). In some cases, $R^3$, $R^4$, $R^5$, and $R^6$ may be the same or different and each may be a leaving groups or a precursor to a vitamin E agent. In some embodiments, upon exposure to a cellular environment, $R^3$, $R^4$, $R^5$, and $R^6$ may dissociate from the platinum center, and at least two new ligands may associate with the platinum center (e.g., $R^7$ and $R^8$, as shown in Equation 1) to form a therapeutically active platinum compound (e.g., [Pt($R^1$)($R^2$)($R^7$)($R^8$)]).

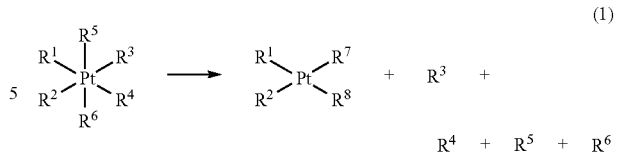

$R^7$ and $R^8$ may be the same or different and may be any suitable ligand as will be known to those of ordinary skill in the art, and are generally ligands or groups present in the environment surrounding the compound during dissociation of $R^3$, $R^4$, $R^5$ and/or $R^6$ (e.g., present in situ and/or in a cellular environment) and are capable of binding to platinum (e.g., water). It should be understood, that in some cases, less than all of $R^3$, $R^4$, $R^5$, and $R^6$ may dissociate from the platinum center and less than two ligands may associate with the platinum center. For example, $R^3$, $R^5$, and $R^6$ may dissociate from the platinum center and $R^8$ may associate, thereby forming a compound having the formula [Pt($R^1$)($R^2$)($R^3$)($R^8$)]. Those of ordinary skill in the art will be able to select appropriate combinations of ligands to form the desired therapeutically active complex. At least one of the ligands that dissociate may be selected such that it forms a vitamin E agent.

Non-limiting examples of $R^1$, $R^2$, $R^3$, $R^4$, $R^5$ and $R^6$ ligands include amines (primary, secondary, and tertiary), aromatic amines, halides, amino groups, amido groups, nitro groups, nitroso groups, amino alcohols, nitriles, imino groups, isonitriles, cyanates, isocyanates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, at least some of the ligands (e.g., $R^1$-$R^4$) may be aryl group, alkenyl group, alkynyl group or other moiety which may bind the metal atom in either a sigma- or pi-coordinated fashion. In some cases, $R^1$ and $R^2$ may be labile ligands and $R^3$ and $R^4$ may be non-labile ligands covalently bonded to the platinum metal center. For example, in some embodiments, at least one of $R^1$, $R^2$, $R^3$, $R^4$, $R^5$ and $R^6$ is a halide (e.g., Cl). In some instances, at least one of $R^1$, $R^2$, $R^3$, $R^4$ is ammonia, an amine, or a heterooocycle. In some embodiments at least one of $R^1$, $R^2$, $R^3$, $R^4$, $R^5$ and $R^6$ is an alkoxy group (e.g., —OC$_2$H$_5$).

In some cases, the at least two ligands are selected such that the ligands are cis to each other (e.g., $R^1$ and $R^2$, $R^1$ and $R^3$, $R^1$ and $R^5$, $R^1$ and $R^6$, $R^2$ and $R^4$, etc.). That is, the at least two ligands may not be trans to each other (e.g., $R^1$ and $R^4$, $R^2$ and $R^3$, $R^5$ and $R^6$). However, in some cases, the ligands may be selected such that they are trans to each other (e.g., in embodiments where the desired therapeutically active platinum compound has two essential ligands which are trans to each other). In some cases, the at least two ligands occupy equatorial positions of the compound. In some instances, however, one or more of the ligands may occupy an axial position of the compound. In some embodiments, more than two ligands may be essential for the formation of a therapeutically active platinum compound and those or ordinary skill in the art will be able to determine the required structure of the composition such that the essential ligands are present.

Accordingly, in some embodiments, at least two $R^1$, $R^2$, $R^3$, $R^4$, $R^5$ and $R^6$ may be the same or different and each is a group comprising at least one of halogen, ammonia, —N(R')

₂, —OR', an aryl group, heteroaryl, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted; each R' is independently hydrogen, alkyl, alkenyl, alkynyl, aryl, heteroaryl, or acyl, any being optionally substituted, or any two R' may be joined together to form a ring; and at least one of the other four ligands may comprise a vitamin E agent, or a second generation precursor to a vitamin E agent, when dissociated from the platinum. The remaining ligands may be leaving groups As a specific example of the above, in some cases, $R^1$ and $R^2$ (e.g., two cis ligands) can be the same or different and each is a group comprising at least one of halogen, ammonia, —$N(R')_2$, —OR', an aryl group, heteroaryl, a heterocycle including at least one nitrogen, or a leaving group, any being optionally substituted, or, any two or three of $R^1$, $R^2$, $R^3$ and $R^4$ can be joined together to form a bidentate ligand or tridentate ligand, any being optionally substituted; each R' is independently hydrogen, alkyl, alkenyl, alkynyl, aryl, heteroaryl, or acyl, any being optionally substituted, or any two R' may be joined together to form a ring; and $R^3$, $R^4$, $R^5$, and $R^6$ may be the same or different and at least one is a vitamin E agent, or a second generation precursor of a vitamin E agent, when dissociated from platinum. In some instances, $R^3$, $R^4$, $R^5$ and/or $R^6$ comprise the same or different vitamin E agent when dissociated form platinum.

In some embodiments, at least one of $R^1$-$R^6$ is a vitamin E agent, when dissociated from the platinum, that affects a cellular pathway of a cancer cell. In some cases, two, three, or four of the ligands are a vitamin E agent (or a second generation precursor to a vitamin E agent), when dissociated from platinum.

In some embodiments, at least one of $R^1$-$R^6$ (e.g., at least one of $R^5$ and $R^6$) is or comprises the group,

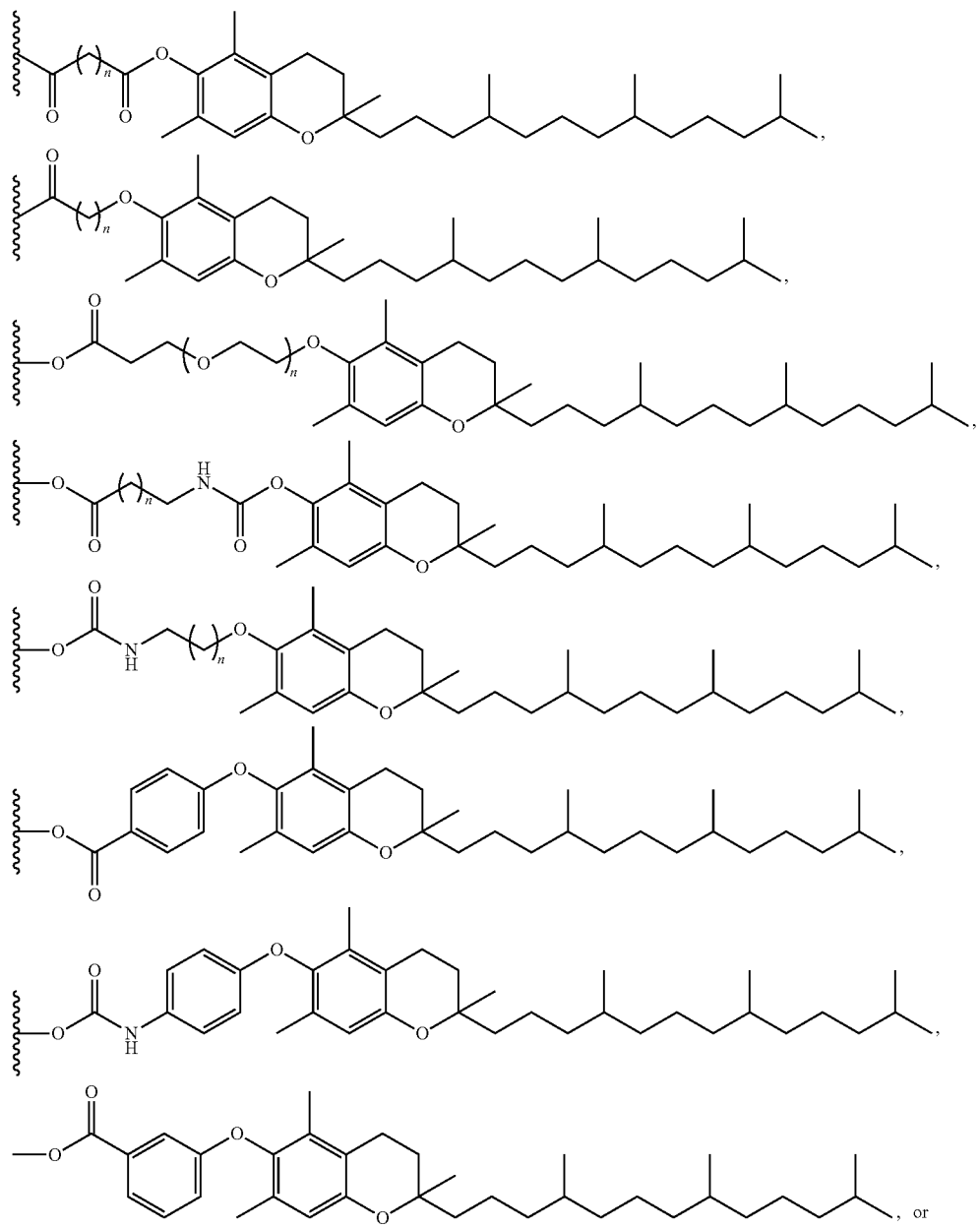

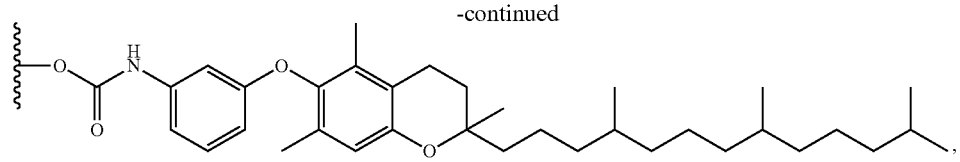

wherein n is 1, 2, 3, 4, 5, or 6,

In some embodiments, at least one of $R^1$-$R^6$ (e.g., at least one of $R^5$ or $R^6$) is or comprises the group:

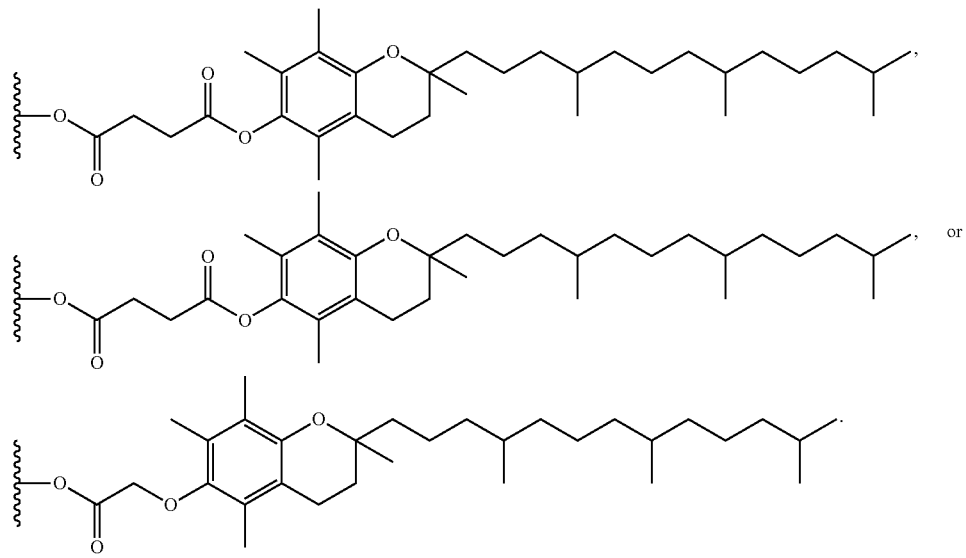

In some embodiments, those of $R^1$-$R^6$ which are not a precursor to a vitamin E agent, may be a leaving group, a non-interfering ligand, and/or a non-interfering group. As used herein, the term "non-interfering group," or "non-interfering ligand" refers to any group or ligand which does not significantly affect or alter the properties of the compound and, in some cases, does not affect or does not significantly affect a cellular pathway of a cancer cell.

Non-limiting examples of compounds of the present invention include:

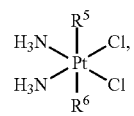

wherein at least one of $R^5$ and $R^6$ is

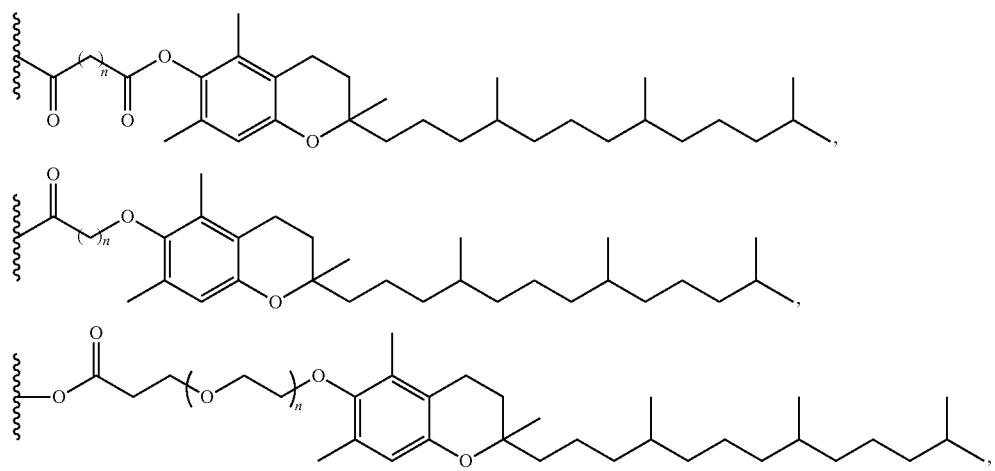

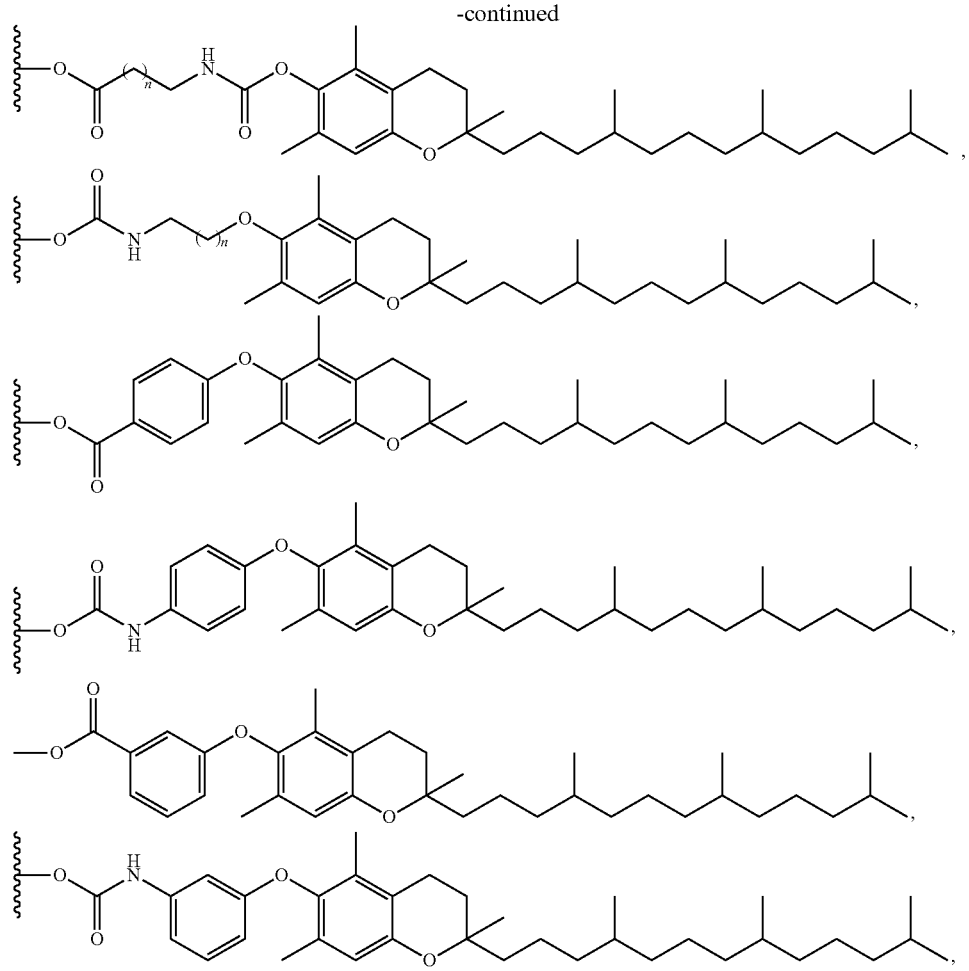
wherein n is 1, 2, 3, 4, 5, or 6, and pharmaceutically acceptable salts thereof. In some embodiment, one of $R^5$ and $R^6$ is a vitamin E agent (e.g., as shown above) and one of $R^5$ and $R^6$ is an alkoxy (e.g., $-OC_2H_5$). In certain embodiments, structures of the compound include:
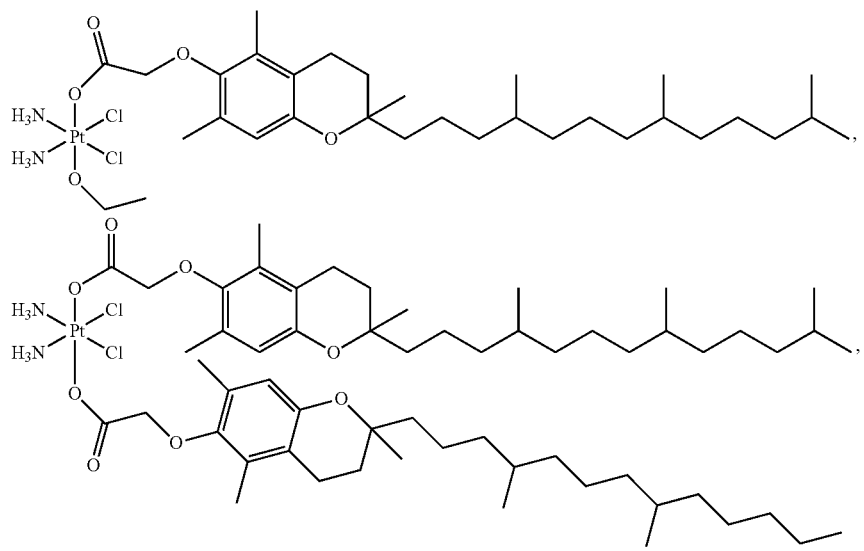

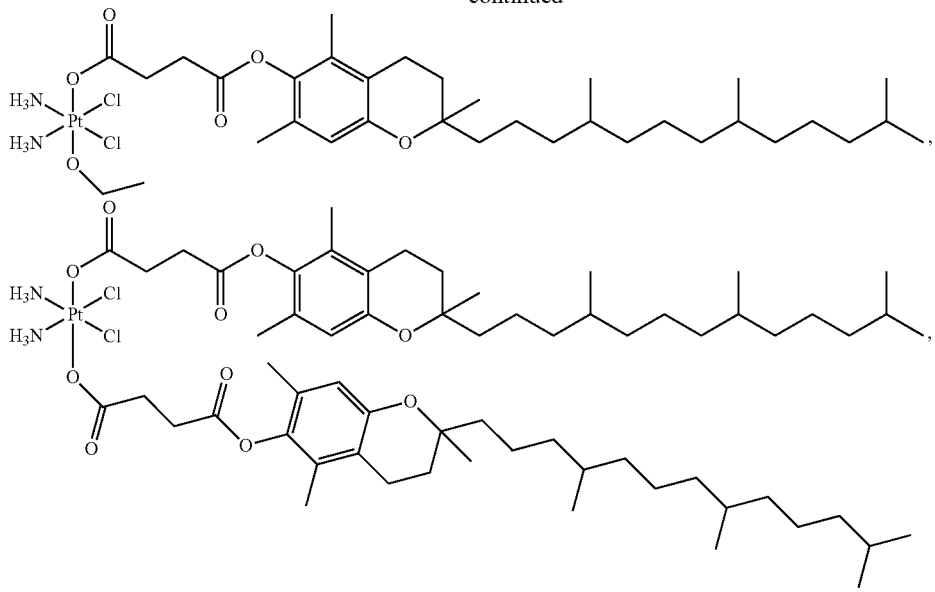

and pharmaceutically acceptable salts thereof.

In some embodiments, the compound may have the formula,

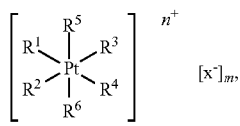

wherein, X is a counterion, and n and m are 1, or n and m are 2, and $R^1$-$R^6$ are as described herein.

The leaving groups, non-interfering groups, and/or precursor to vitamin E agents (e.g., in some cases, $R^5$ and $R^6$, in other cases, $R^3$, $R^4$, $R^5$, and $R^6$, etc.) may be covalently bound to the platinum center or may be associated with the platinum center via a tether. In some embodiments, at least one of these ligands (e.g., $R^3$, $R^4$, $R^5$ and/or $R^6$) may be released from the platinum(IV) center and a platinum (II) complex may form. In some cases, as discussed in more detail herein, the tether may comprise ester linkers that covalently link the vitamin E agent to the platinum center. The tether may be hydrolyzed, in some cases, by intracellular esterases and the vitamin E agent may be formed (e.g., dissociated from the platinum center and without coordination to a tether). In some cases, however, the vitamin E agent may be therapeutically active when it comprises the tether (e.g., when the tether remains associated with the vitamin E agent).

In some cases, at least two of the ligands (e.g., $R^3$, $R^4$, $R^5$, and/or $R^6$) may comprise the same or different precursor to a vitamin E agent. For example, $R^5$ may comprise a precursor to a first vitamin E agent, and $R^6$ may comprise a precursor to a second vitamin E agent. As another example, $R^5$ and $R^6$ may be different and $R^5$ (or $R^6$) may comprise a precursor to a vitamin E agent, and $R^6$ (or $R^5$) may comprise a non-vitamin E agent (e.g., —$OC_2H_5$).

In some embodiments, the precursor to the vitamin E agent may either be directly attached (e.g., via a covalent bond) to the platinum center or attached to the platinum through a tether. When the therapeutic agent is not coordinated directly to the metal center, a variety of tethers can be used to link the therapeutic agent to the metal center. For example, the tether may be a hydrocarbon chain of various possible lengths containing at least one functional group which allows for release of the therapeutic agent under the right conditions. Non-limiting examples of functional groups which can be used in tethers include esters, amides, amines, ethers, ureas, carbamates, carbonates, and anhydride moieties. In general, the tether may be any suitable molecule that allows the vitamin E agent to be associated with and dissociated from the platinum center, e.g., in response to a redox change.

In some embodiments, release of at least one ligand (e.g., $R^3$, $R^4$, $R^5$ and/or $R^6$, or in some cases, $R^5$ and $R^6$, etc.) from the platinum(IV) therapeutically active precursor may form a platinum(II) therapeutically active agent or a second generation precursor to a platinum(II) therapeutically active agent. In some cases, one, two, three, or four of $R^3$, $R^4$, $R^5$ and/or $R^6$ may be released from the platinum(IV) therapeutically active precursor, thereby forming a platinum(II) therapeutically active agent. In some cases, as described herein, one or more ligands or groups (e.g., $R^7$ and/or $R^8$, as described herein) may associate with the platinum(II) therapeutically active agent upon dissociation of the one or more ligands. The therapeutically active platinum(II) agent may be useful for the treatment proliferative diseases (e.g., cancer). In some cases, the release of at least one ligand (e.g., $R^5$ and $R^6$) from the platinum center may be facilitated by a redox change of the platinum(IV) center. In some instances, axial ligands may be released due to the nature of the axial bonds. In some cases, the redox change may be caused by the release of $R^5$ and $R^6$ from the platinum(IV) center. In other cases, a redox change of the platinum(IV) center may promote the release of $R^5$ and $R^6$. For example, a redox change of the platinum(IV) center may cause a change in coordination geometry for the metal ion that reduces the number of ligands, thereby causing $R^5$ and $R^6$ to dissociate from the metal center. As another example, the redox change of a platinum(IV) center may promote the lability of one or more ligands (e.g., $R^3$, $R^4$, $R^5$, and/or $R^6$) and make it more likely that the one or more ligands (e.g., $R^3$, $R^4$, $R^5$, and/or $R^6$) may be replaced by other ligands.

In some cases, the precursor to a therapeutically active agent may form, upon release, a therapeutically active agent or a second generation precursor to a therapeutically active agent. The second generation precursor to a therapeutically active agent may be chemically altered, transformed, and/or activated after release from the compound (e.g., upon reduction of a Pt(IV) center to a Pt(II) center) to form the therapeutically active agent. For example, the second generation precursor to a vitamin E agent may comprise a functional group (e.g., a portion of the tether) which may undergo a chemical reaction (e.g., in situ, upon exposure to a cellular environment) to form a vitamin E agent. As a specific non-limiting example, the second generation precursor may comprise an acyl or carbonyl group, which may undergo transformation in situ to form an alcohol or ester, which may be a therapeutically active composition. As another example, the replacement of a ligand on a second generation precursor of a therapeutically active platinum compound may form a therapeutically active platinum compound.

In some embodiments, the release rate of the vitamin E agent (or precursor) from the platinum(IV) compound may be altered based on the nature of the vitamin E agent and/or by altering the tether used in association of the vitamin E agent with the platinum center. This may be due to a change in the redox properties of the platinum center. For example, a first $R^5$ group may allow for the reduction of the Pt(IV) center more readily than a second $R^5$ group, which may lead to the release of the first $R^5$ group (e.g., a vitamin E agent) at a different rate than the release of the second $R^5$ group. In one embodiment of the present invention, the release rate of a selected vitamin E agent may be adjusted by modifying the nature of the tether (e.g., the type of functional group, carbon chain length, etc.).

In some embodiments, the ligands of the composition may be selected such that upon reduction of the metal center, one or more ligands may be released and selected platinum(II) therapeutically active agent or second generation precursor to a platinum(II) therapeutically active agent is formed. For example, $R^1$, $R^2$, $R^3$, and $R^4$ may be selected such that, upon reduction of the platinum metal center and release of $R^5$ and $R^6$ (as described herein), a selected platinum(II) therapeutically active agent is formed. As another example, $R^1$, $R^2$, may be selected such that, upon reduction of the platinum metal center, release of $R^3$, $R^4$, $R^5$ and $R^6$, and association of $R^7$ and $R^8$ (as described herein), a selected platinum(II) therapeutically active agent is formed. The therapeutically active platinum(II) agent may be any known platinum(II) therapeutically active agent. Non-limiting examples of platinum(II) therapeutically active agents include cisplatin ([cis-Pt(NH$_3$)$_2$Cl$_2$]), carboplatin ([cis-Pt(NH$_3$)$_2$(1,1-(OCO)$C_4H_6$)]), oxaliplatin, [cis-Pt(NH$_3$)$_2$(trans-1,2-(OCO)$_2C_6H_{10}$)], [cis-Pt(DACH)Cl$_2$] (where DACH is diaminocyclohexane), nedaplatin ([cis-Pt(NH$_3$)$_2$OCH$_2$CHO$_2$], stratoplatin, paraplatin, platinol, cycloplatam, dexormaplatin, enloplatin, iproplatin, lobaplatin, ormaplatin, spiroplatin, zeniplatin, etc., as will be known to those of ordinary skill in the art.

In some embodiments, the ligands associated with the platinum center in the therapeutically active platinum compound (e.g., $R^1$-$R^4$) may include functional groups capable of interaction with a metal center, e.g., heteroatoms such as nitrogen, oxygen, sulfur, and phosphorus. Non-limiting examples of compounds which the ligands may comprise include amines (primary, secondary, and tertiary), aromatic amines, amino groups, amido groups, nitro groups, nitroso groups, amino alcohols, nitriles, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, at least some of the ligands (e.g., $R^1$-$R^4$) may be aryl group, alkenyl group, alkynyl group or other moiety which may bind the metal atom in either a sigma- or pi-coordinated fashion. In some cases, $R^1$ and $R^2$ may be labile ligands and $R^3$ and $R^4$ may be non-labile ligands covalently bonded to the platinum metal center.

In some embodiments, any two or three of $R^1$, $R^2$, $R^3$, and $R^4$ can be joined together to form a bidentate ligand or tridentate ligand. A bidentate ligand when bound to a metal center, forms a metallocycle structure with the metal center. Bidentate ligands suitable for use in the present invention include species which have at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the invention include, but are not limited to, alkyl and aryl derivatives of moieties such as amines, phosphines, phosphites, phosphates, imines, oximes, ethers, hybrids thereof, substituted derivatives there of, aryl groups (e.g., bis-aryl, heteroaryl-substituted aryl), heteroaryl groups, and the like. Specific examples of bidentate ligands include ethylene diamine, 2,2'-bipyridine, acetylacetonate, oxalate, and the like. Non-limiting examples of bidentate ligands include diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

In some embodiments, compounds of the invention may comprise a tridentate ligand, which includes species which have at least three sites capable of binding to a metal center. For example, the tridentate ligand may comprise at least three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties, triimidazoyl moieties, tris pyrazoyl moieties, and combinations of the above ligands.

Pt(II) and Pt(IV) complexes of the invention may be synthesized according to methods known in the art, including various methods described herein. For example, the method may comprise reaction of cisplatin with one or more ligand sources. In some cases, a Pt(IV) complex, wherein $R^5$ and $R^6$ are —OH, can be obtained by reaction of the parent Pt(II) species with, for example, hydrogen peroxide at temperatures ranging between about 25 and about 60° C. in an appropriate solvent, such as water or N,N-dimethylformamide. The desired Pt(IV) complex may synthesized comprising selected $R^5$ and $R^6$ groups according to method known in the art, for example, by functionalization of the —OH groups (e.g., by reaction with an anhydride, an isocyanate, a pyrocarbonate, an acid chloride, etc.).

In some embodiments, a platinum complex may comprise one or more leaving groups. As used herein, a "leaving group" is given its ordinary meaning in the art and refers to an atom or a group capable of being displaced by a nucleophile. Examples of suitable leaving groups include, but are not limited to, halides (such as chloride, bromide, and iodide), pyridine, alkanesulfonyloxy, arenesulfonyloxy, alkyl-carbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. A leaving group may also be a bidentate, tridentate, or other multidentate ligand. In some embodiments, the leaving group is a halide or carboxylate. In some embodiments, the leaving group is chloride.

Some embodiments of the invention comprise compounds having two leaving groups positioned in a cis configuration, i.e., the compound may be a cis isomer. However, it should be understood that compounds of the invention may also have two leaving groups positioned in a trans configuration, i.e., the compound may be a trans isomer. Those of ordinary skill in the art would understand the meaning of these terms.

Some embodiments of the invention provide the compound as a salt comprising a positively-charged platinum complex and a counterion (e.g., "X"). The counterion X may be a weak or non-nucleophilic stabilizing ion. In some cases, the counterion is a negatively-charged and/or non-coordinating ion. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, and the like), $BF_4^-$, $PF_4^-$, $PF_6^-$, $SbF_6^-$, $B[3,5\text{-}(CF_3)_2C_6H_3]_4^-$, $BPh_4^-$, $Al(OC(CF_3)_3)_4^-$, and a carborane anion (e.g., $CB_{11}H_{12}^-$ or $(HCB_{11}Me_5Br_6)^-$).

The invention also comprises homologs, analogs, derivatives, enantiomers, diastereomers, tautomers, cis- and trans-isomers, and functionally equivalent compositions of compounds described herein. "Functionally equivalent" generally refers to a composition capable of treatment of patients having cancer, or of patients susceptible to cancers. It will be understood that the skilled artisan will be able to manipulate the conditions in a manner to prepare such homologs, analogs, derivatives, enantiomers, diastereomers, tautomers, cis- and trans-isomers, and functionally equivalent compositions. Homologs, analogs, derivatives, enantiomers, diastereomers, tautomers, cis- and trans-isomers, and functionally equivalent compositions which are about as effective or more effective than the parent compound are also intended for use in the method of the invention. Such compositions may also be screened by the assays described herein for increased potency and specificity towards a cancer, preferably with limited side effects. Synthesis of such compositions may be accomplished through typical chemical modification methods such as those routinely practiced in the art. Another aspect of the present invention provides any of the above-mentioned compounds as being useful for the treatment of cancer.

The invention further comprises compounds, compositions, preparations, formulations, kits, and the like, comprising any of the compounds as described herein. In some cases, treatment of a cancer may involve the use of compounds and/or compositions, as described herein. That is, one aspect of the invention involves a series of compositions (e.g., pharmaceutical compositions) or agents useful for treatment of cancer or tumor. These compositions may also be packaged in kits, optionally including instructions for use of the composition for the treatment of such conditions. These and other embodiments of the invention may also involve promotion of the treatment of cancer or tumor according to any of the techniques and compositions and combinations of compositions described herein.

Aspects of the invention may be used to prevent the growth of a tumor or cancer, and/or to prevent the metastasis of a tumor or cancer. In some embodiments, compounds and/or compositions of the invention may be used to shrink or destroy a cancer. It should be appreciated that compounds and/or compositions of the invention may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition of the invention may be administered to a patient who has undergone a treatment involving surgery, radiation, and/or chemotherapy. In certain embodiments, a composition of the invention may be administered chronically to prevent, or reduce the risk of, a cancer recurrence.

In another aspect, the present invention provides "pharmaceutical compositions" or "pharmaceutically acceptable" compositions, which comprise a therapeutically effective amount of one or more of the compounds described herein, formulated together with one or more pharmaceutically acceptable carriers (additives) and/or diluents. As described herein, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain one or more basic functional groups and, thus, are capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," *J. Pharm. Sci.* 1977, 66, 1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compound may be orally administered, parenterally administered, subcutaneously administered, and/or intravenously administered. In certain embodiments, a compound or pharmaceutical preparation is administered orally. In other embodiments, the compound or pharmaceutical preparation is administered intravenously. Alternative routes of administration include sublingual, intramuscular, and transdermal administrations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with the present invention include time-release, delayed release, sustained release, or controlled release delivery systems, as described herein. Such systems may avoid repeated administrations of the active compounds of the invention in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The formulation may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiment of the invention.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, about 0.1% to about 99.5%, about 0.5% to about 90%, or the like, of active ingredient in combination with a pharmaceutically acceptable carrier.

The administration may be localized (i.e., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat cancer. An effective amount is generally an amount sufficient to inhibit cancer within the subject.

One of skill in the art can determine what an effective amount of the composition is by screening the ability of the composition using any of the assays described herein. The effective amounts will depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments may involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. In some cases, the dose may range from between about 5 and about 50 mg of compound per kg of body weight, between about 10 and about 40 mg of compound per kg of body weight, between about 10 and about 35 mg of compound per kg of body weight, or between about 15 and about 40 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it may be administered as a pharmaceutical formulation (composition) as described above.

The present invention also provides any of the above-mentioned compounds and compositions useful for treatment of cancer packaged in kits, optionally including instructions for use of the composition for the treatment of cancer. That is, the kit can include a description of use of the composition for participation in any biological or chemical mechanism disclosed herein associated with cancer or tumor. The kits can further include a description of activity of cancer in treating the pathology, as opposed to the symptoms of the cancer. That is, the kit can include a description of use of the compounds and/or compositions as discussed herein. The kit also can include instructions for use of a combination of two or more compounds and/or compositions of the invention. Instructions also may be provided for administering the drug by any suitable technique, such as orally, intravenously, or via another known route of drug delivery. The invention also involves promotion of the treatment of cancer according to any of the techniques and compounds and composition combinations described herein.

The compounds and/or compositions of the invention, in some embodiments, may be promoted for treatment of abnormal cell proliferation, cancers, or tumors, or includes instructions for treatment of accompany cell proliferation, cancers, or tumors, as mentioned above. In another aspect, the invention provides a method involving promoting the prevention or treatment of cancer via administration of any one of the compounds and/or compositions of the present invention, and homologs, analogs, derivatives, enantiomers and functionally equivalent compounds and/or compositions thereof in which the composition is able to treat cancers. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compounds and/or compositions of the invention in connection with treatment of cell proliferation, cancers or tumors. "Instructions" can define a component of promotion, and typically involve written instructions on or associated with packaging of compounds and/or compositions of the invention. Instructions also can include any oral or electronic instructions provided in any manner. The "kit" typically defines a package including any one or a combination of the compounds and/or compositions of the invention and the instructions, or homologs, analogs, derivatives, enantiomers and functionally equivalent compounds and/or compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules, and/or particles as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compounds and/or compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compounds and/or compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As used herein, a "subject" or a "patient" refers to any mammal (e.g., a human), such as a mammal that may be susceptible to tumorigenesis or cancer. Examples include a human, a non-human primate, a cow, a horse, a pig, a sheep, a goat, a dog, a cat, or a rodent such as a mouse, a rat, a hamster, or a guinea pig. Generally, or course, the invention is directed toward use with humans. A subject may be a subject diagnosed with cancer or otherwise known to have cancer. In certain embodiments, a subject may be selected for treatment on the basis of a known cancer in the subject. In some embodiments, a subject may be selected for treatment on the basis of a suspected cancer in the subject. In some embodiments, a cancer may be diagnosed by detecting a mutation associate in a biological sample (e.g., urine, sputum, whole blood, serum, stool, etc., or any combination thereof. Accordingly, a compound or composition of the invention may be administered to a subject based, at least in part, on the fact that a mutation is detected in at least one sample (e.g., biopsy sample or any other biological sample) obtained from the subject. In some embodiments, a cancer may not have been detected or located in the subject, but the presence of a mutation associated with a cancer in at least one biological sample may be sufficient to prescribe or administer one or more compounds or compositions of the invention to the subject. In some embodiments, the composition may be administered to prevent the development of a cancer. However, in some embodiments, the presence of an existing cancer may be suspected, but not yet identified, and a composition of the invention may be administered to prevent further growth or development of the cancer.

It should be appreciated that any suitable technique may be used to identify or detect mutation and/or over-expression associated with a cancer. For example, nucleic acid detection techniques (e.g., sequencing, hybridization, etc.) or peptide detection techniques (e.g., sequencing, antibody-based detection, etc.) may be used. In some embodiments, other techniques may be used to detect or infer the presence of a cancer (e.g., histology, etc.).

The presence of a cancer can be detected or inferred by detecting a mutation, over-expression, amplification, or any combination thereof at one or more other loci associated with a signaling pathway of a cancer.

A "sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The phrase "therapeutically effective amount" as used herein means that amount of a compound, material, or composition comprising a compound of the present invention which is effective for producing some desired therapeutic effect in a subject at a reasonable benefit/risk ratio applicable to any medical treatment. Accordingly, a therapeutically effective amount prevents, minimizes, or reverses disease progression associated with a cancer. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more compounds may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more compounds described herein in an amount effective to treat one or more cancers described herein.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "aralkyl" or "arylalkyl," as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence. An example of a substituted amine is benzylamine. Another non-limiting example of an amine is cyclohexylamine.

As used herein, the term "phosphine" is given its ordinary meaning in the art and refers to a group comprising at least one phosphorus atom. The phosphorus atom may bear one, two, or three aliphatic or aromatic groups, optionally substituted and optionally comprising at least one heteroatom.

As used herein, the term "phosphono" refers to the group —O(P=O)(OR$^{cc}$)R$^{aa}$, wherein each instance of R$^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SS-R$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The following reference is herein incorporated by reference: U.S. Provisional Patent Application Ser. No. 61/779, 832, filed Mar. 13, 2013, entitled "Vitamin E Analogs Conjugated Pt(IV) Complexes as Dual Targeting Anticancer Agents," by Lippard, et al.

The following examples are intended to illustrate certain embodiments of the present invention, but do not exemplify the full scope of the invention.

EXAMPLES

Example 1

Platinum-based anticancer agents induce apoptosis by damaging nuclear DNA in cancer cells. Following the success of cisplatin over the past few decades, platinum(II) analogues, including carboplatin, oxaliplatin, nedalplatin, and lobaplatin, have been introduced into the clinic to treat various cancers. Despite their efficacy, the inherent side effects and limitations of platinum(II) compounds remain problematic. Platinum(IV) prodrugs offer a viable alternative to platinum(II) therapy. Surrounded by six ligands in an octahedral coordination environment, the platinum(IV) metal center is more inert toward substitution reactions than platinum(II). Upon reduction, two axial ligands are released and the corresponding divalent species is generated. Chemical modification of the axial ligands can significantly influence the efficacy and pharmacokinetics of platinum(IV) agents. Single agents with dual-targeting capabilities provide a powerful approach to attack cancer cells.

In this example, a vitamin E analog, α-tocopherol succinate (α-TOS) was used as the axial ligand(s) in order to achieve a better match in activity between the intracellular reduction products. Two platinum(IV) complexes were constructed for simultaneously targeting of genomic DNA and mitochondria. α-TOS displayed potent in vitro cytotoxicity in a variety of cancer cell types including prostate, breast, lung, and colon cells. α-TOS inhibits anti-apoptotic proteins, Bcl-2 and Bcl-xL, thereby inducing mitochondria-mediated apoptotic cell death.

The Pt(IV) design adopted here was based on the following premises: (1) α-TOS is highly lipophilic and will facilitate cellular uptake of Pt(IV); (2) α-TOS has an $IC_{50}$ value in the micromolar range, comparable to that of platinum(II) complexes; (3) intracellular reduction or aquation of the Pt(IV) complexes is likely to release α-TOS, which will inhibit Bcl-xL and disrupt mitochondrial function, and cisplatin, which will target nuclear DNA. Together these effects were expected to induce apoptosis in a "dual-threat" manner.

Pt(IV)(α-TOS)$_2$ and Pt(IV)(α-TOS)(OEt) were prepared in a single step in reactions of c,c,t-[Pt(NH$_3$)$_2$Cl$_2$(OH)$_2$] and c,c,t-[Pt(NH$_3$)$_2$Cl$_2$(OH)(OEt)], respectively, with the acid anhydride derivative of α-TOS as shown in Scheme 1. The high lipophilicity of the final compounds facilitated isolation through precipitation from methanol or by silica column chromatography. Both Pt(IV)(α-TOS)$_2$ and Pt(IV)(α-TOS)(OEt) were fairly insoluble in water, but readily dissolved in organic solvents such as dimethyl formaldehyde, dimethyl sulfoxide, and chloroform. The final compounds were characterized by 1H, 13C, and 195Pt NMR spectroscopy, ESI-MS, and elemental analysis.

Scheme 1: Synthesis of the vitamin E analog, a-TOS, conjugated Pt(IV) complexes: Pt(IV)(α-TOS)$_2$ and Pt(IV)(α-TOS)(OEt)

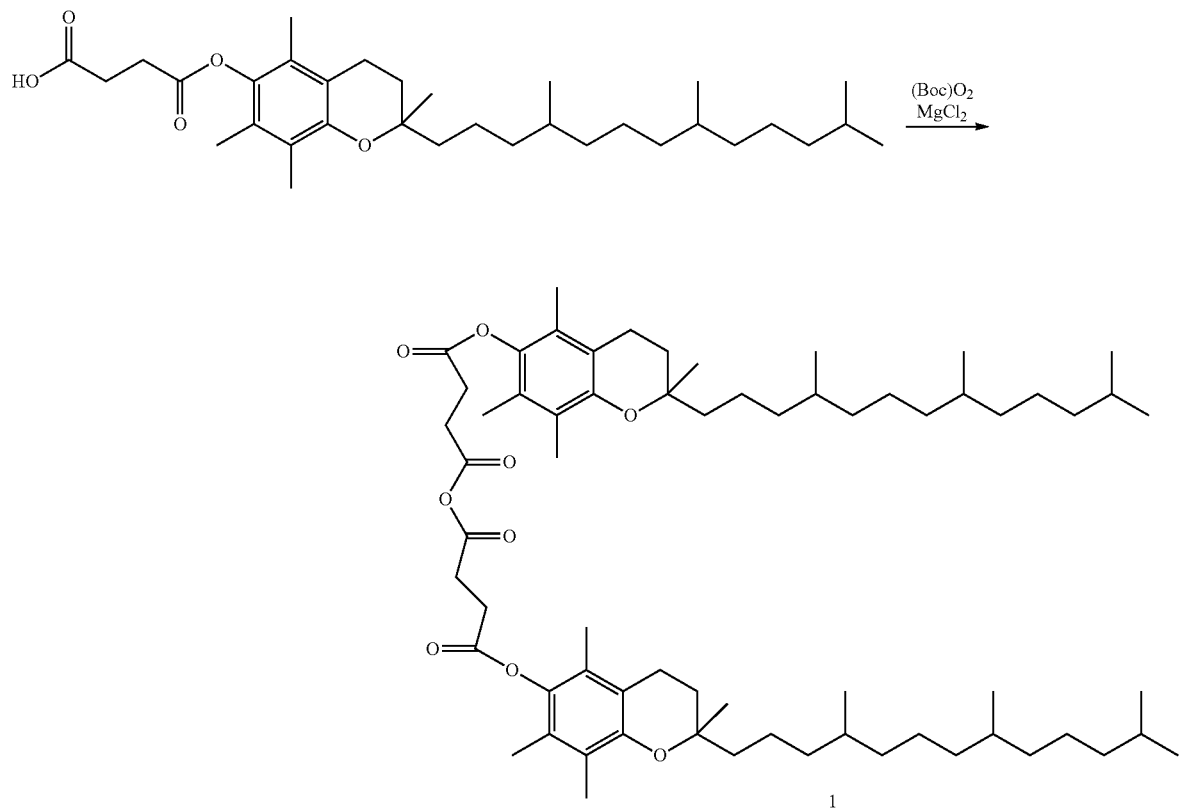

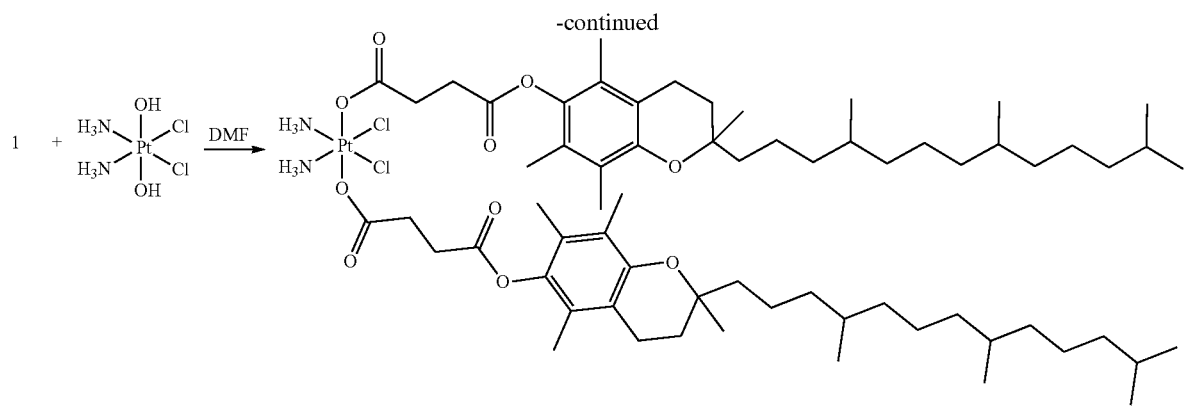

Pt(IV)(α-TOS)₂

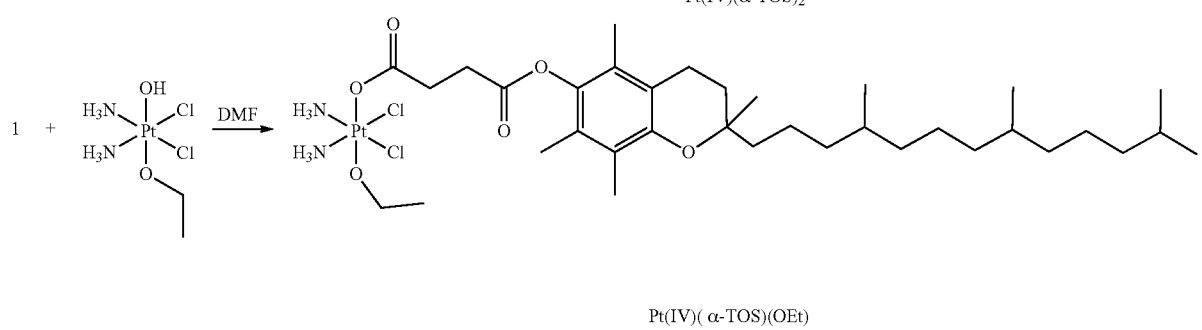

Pt(IV)(α-TOS)(OEt)

Example 2

This example describes the anti-proliferative and cellular uptake properties of vitamin E analogs conjugated to Pt(IV) complexes.

The anti-proliferative properties of Pt(IV)(α-TOS)(OEt), Pt(IV)(α-TOS)₂, α-TOS, Pt(IV)(OAc)₂, cisplatin, mixtures of α-TOS and cisplatin were evaluated by the MTT assay and the results are summarized in Table 1. Pt(IV)(OAc)₂ is known to be non-therapeutically active and was used as a control platinum (IV) compound. Pt(IV)(α-TOS)(OEt) exhibited impressive potency, 7-220 times greater than that of cisplatin or combinations of cisplatin and α-TOS, across several tumour cell lines. Encouragingly Pt(IV)(α-TOS)(OEt) exhibited lower toxicity against healthy cells. Notably, a 265-fold reduction in toxicity was observed for non-tumorigenic lung fibroblast cells (MRC-5) compared to ovarian carcinoma cells (A2780). The difference in toxicities of Pt(IV)(α-TOS)₂ and Pt(IV)(α-TOS)(OEt) can be attributed to their differing lipophilities and, consequently, bioavailability. Pt(IV)(α-TOS)₂ is highly lipophilic and thus susceptible to detoxification through sequestration by extra- or intra-cellular proteins and entrapment inside the cell membrane. Pt(IV)(OAc)₂, bearing biologically inactive acetate ligands, exhibited low toxicity ($IC_{50}$>100 μM) against all cell lines. This emphasized the important contribution of α-TOS towards the potency of Pt(IV)(α-TOS)(OEt).

TABLE 1

The cytotoxicity of Pt(IV) complexes in cancer and non-cancer cell lines by $IC_{50}$ (μM).

| Cell name | Type | CisPt | α-Tos | CisPt + α-Tos | Pt(IV)(α-Tos)(OEt) | Pt(IV)(α-Tos)₂ | Pt(IV)(OAc)₂ |
|---|---|---|---|---|---|---|---|
| A549 | Lung | 2.5(0.8) | 26.9(1.4) | 6.4(0.2) | 1.3(0.1) | 13.9(0.1) | — |
| HeLa | Cervical | 1.4(0.3) | 25.1(1.0) | 3.4(0.5) | 1.9(0.3) | 24.7(0.6) | — |
| A2780 | Ovarian | 0.56 | 13.8(1.08) | 4.4(1.2) | 0.02(0.01) | 56.4(4.6) | — |
| A2780/CP70 | Ovarian (CisPt resistant) | 6.0 | 21.7(1.7) | 7.3(0.6) | 1.1(0.1) | >100 | — |
| PC-3 | Prostate | 15.1(0.9) | 37.0(0.1) | 19.2(0.2) | 2.5(0.2) | >100 | >100 |
| HCT116 | Colon | 6.6(0.4) | 31.2(1.8) | 17.3(0.9) | 1.24(0.01) | >100 | >100 |
| MCF-7 | Breast | 18.2(0.5) | 40.5(5.0) | 18.3(0.5) | 5.9(0.1) | >100 | >100 |
| MRC-5 | Lung Normal | 6.3(0.4) | 28.5(4.2) | 18.8(0.7) | 5.3(0.2) | 80.5(0.6) | >100 |

Figure 1B:
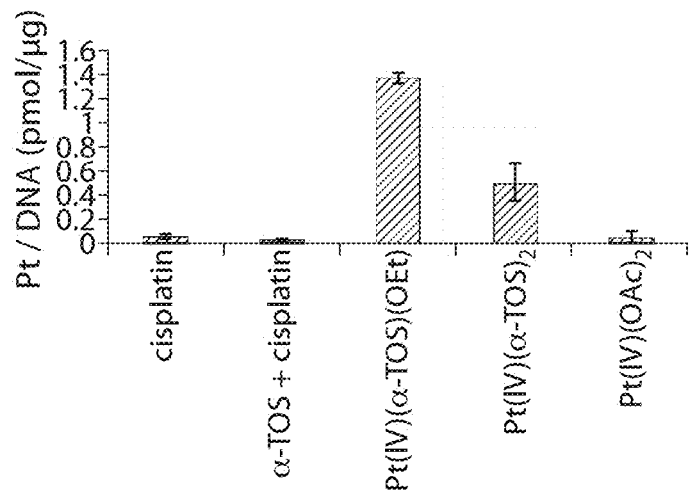

Cellular uptake studies were performed to measure the distribution of platinum species in different subcellular compartments. A549 cells were treated with 10 μM Pt(IV)(α-TOS)₂, Pt(IV)(α-TOS)(OEt), or cisplatin for 3 hours and the cells were fractionated into three pools: membrane, nucleus, and cytosol. FIG. 1A shows the cell uptake of Pt(IV)(α-TOS)₂, Pt(IV)(α-TOS)(OEt), and cisplatin in A549 cells. The platinum levels in each pool were measured by graphite-furnace atomic absorption spectroscopy (GF-AAS). FIG. 1B shows the platinum content in genomic DNA extracted from A549 cells treated with 10 µM of cisplatin, mixtures of α-TOS and cisplatin, Pt(IV)(α-TOS)$_2$, Pt(IV)(α-TOS)(OEt), and Pt(IV)(OAc)$_2$ for 3 hours. Both Pt(IV) agents showed 15-20 times greater cellular uptake than cisplatin. Without being bound by theory it is believed that this property could be due to their higher intrinsic lipophilicity.

Nuclear DNA from A549 cells treated with cisplatin, mixtures of α-TOS and cisplatin, Pt(IV)(α-TOS)$_2$, Pt(IV)(α-TOS)(OEt), and Pt(IV)(OAc)$_2$ (10 µM for 3 hours) were extracted and the platinum content was determined by GF-AAS (see, FIG. 1B). Genomic DNA extracted from cells dosed with Pt(IV)(α-TOS)$_2$ and Pt(IV)α-TOS)(OEt) displayed significantly (t test, $p<0.005$) higher levels of platinum (7-20 fold) than those exposed to cisplatin, mixtures of α-TOS and cisplatin, or Pt(IV)(OAc)$_2$. Therefore the Pt(IV)-α-TOS conjugates were more adept at targeting nuclear DNA than cisplatin or Pt(IV) agents with biological inactive ligands.

Example 3

Figure 2:
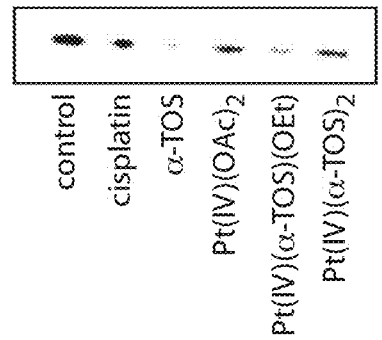
FIG. 2 shows a protein immunoblot for Bax expression after treatment with cisplatin, mixtures of α-TOS and cisplatin, Pt(IV)(α-TOS)$_2$, Pt(IV)(α-TOS)(OEt), and Pt(IV)(OAc)$_2$ at the respective IC$_{50}$ values for 48 hours.
Figure 3:
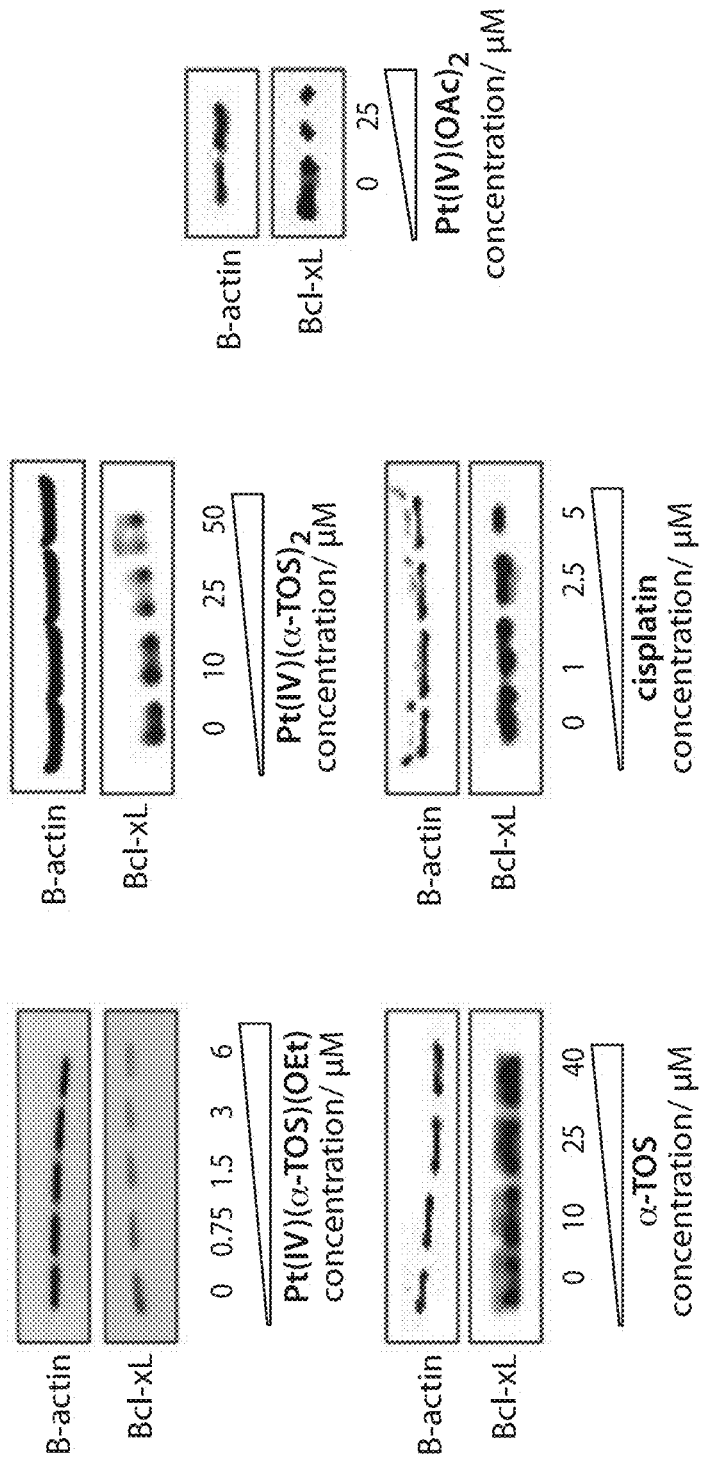
FIG. 3 shows protein immunoblots for B-actin and Bcl-xL expression after treatment with cisplatin, mixtures of α-TOS and cisplatin, Pt(IV)(α-TOS)2, Pt(IV)(α-TOS)(OEt), and Pt(IV)(OAc)$_2$.

This example describes the mechanism of action of the vitamin E analogs conjugated to Pt(IV) complexes.

α-TOS is known to disrupt Bcl-xL-Bax interactions, activate Bax, and thus mediate mitochondrial centered apoptotic cell death. Co-immunoprecipitation studies were carried out to determine whether the Pt(IV)-α-TOS conjugates could behave in a similar manner. To probe the Bcl-xL-Bax interaction dynamics, A549 cells were incubated with α-TOS, cisplatin, Pt(IV)(α-TOS)$_2$, Pt(IV)(α-TOS)(OEt), and Pt(IV)(OAc)$_2$ at the respective IC$_{50}$ values for 48 h, the cell lysates were then subjected to immunoprecipitation with Bcl-xL antibody, and, finally, the immunoprecipitates were probed for Bax content using immunoblotting. The results are shown in FIG. 2. FIG. 3 shows immunoblotting analysis of Bcl-xL expression upon cisplatin, mixtures of α-TOS and cisplatin, Pt(IV)(α-TOS)$_2$, Pt(IV)(α-TOS)(OEt), and Pt(IV)(OAc)$_2$ treatment. As expected, upon α-TOS treatment, the level of Bax associated to the Bcl-xL immunoprecipitate was markedly lower than the untreated control. Pt(IV)(α-TOS)(OEt) treatment also led to reduced Bcl-xL-Bax interactions; moreover, the inhibitory effect was comparable to that of α-TOS treatment. Bcl-xL-Bax interactions were less affected by cisplatin, Pt(IV)(α-TOS)$_2$, or Pt(IV)(OAc)$_2$ incubation. Additional immunoblotting studies were carried to determine the effect of Pt(IV)(α-TOS)(OEt) treatment on transcription. Remarkably, Pt(IV)(α-TOS)(OEt) induced a reduction in Bcl-xL expression. A similar trend was observed for cisplatin, Pt(IV)(α-TOS)$_2$, and Pt(IV)(OAc)$_2$ but not α-TOS. Overall Pt(IV)(α-TOS)(OEt) was able to (1) downregulate Bcl-xL expression and (2) inhibit the interaction of Bcl-xL with Bax, a prerequisite for mitochondrial dysfunction. The former is inherent to cisplatin but not α-TOS, and the latter was inherent to α-TOS but not cisplatin. Pt(IV)(α-TOS)(OEt) was able to combine properties intrinsic to cisplatin and α-TOS, and thereby display transcriptional and post-transcriptional effects superior to α-TOS or cisplatin alone.

Figure 4A:
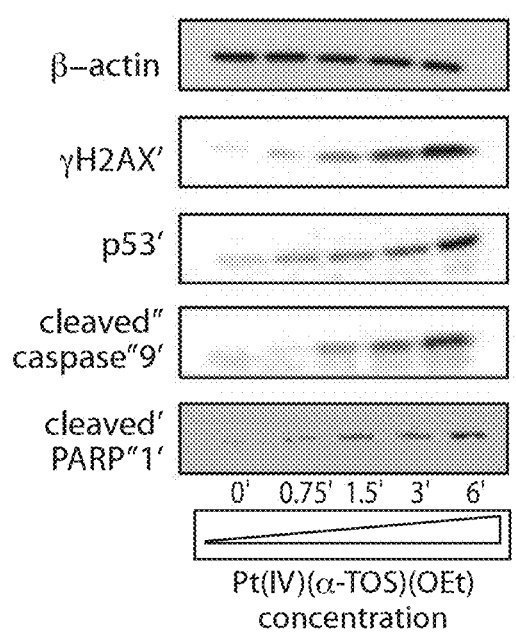
FIGS. 4A-C show (A) protein immunoblots for expression of γH2AX, p53, and cleaved caspase-7, cleaved caspase-9, cleaved PARP-1, and β-actin in A549 cells following treatment with Pt(IV)(OEt)(α-TOS) at 0, 0.75, 1.25, 3, 6 μM for 48 hours, (B) fluorescence microscope images of A549 cells treated with Pt(IV)(α-TOS)(OEt), and (C) histograms, produced from flow cytometry data, representing the change in FL1-H for cells stained with JC-1 in absence (line 1) and presence (line 2) of cisplatin (top) and Pt(IV)(α-TOS)(OEt) (bottom)

To gain further insight into the cellular response evoked by Pt(IV)(α-TOS)(OEt) treatment, biomarkers related to DNA damage and apoptosis were monitored. In the event of DNA damage, γH2AX, the phosphorylated form of histone H2AX, is upregulated upon activation by the apical kinases, ATM and ATR. FIG. 4A shows the protein expression in A549 cells following treatment with Pt(IV)(OEt)(α-TOS) at 0, 0.75, 1.25, 3, 6 µM for 48 h. Whole cell lysates were resolved by SDS-PAGE and analyzed by immunoblotting against γH2AX, p53, and cleaved caspase-7, cleaved caspase-9, cleaved PARP-1, and β-actin as control. After treatment with increasing concentrations (0.75-6 µM) of Pt(IV)(α-TOS)(OEt) for 48 h, A549 cells showed an increase in γH2AX expression, indicative of genomic DNA damage. The expression of p53, a downstream effector of DNA damage, also increased in a dose-dependent manner. In addition, expression levels of apoptosis-related proteins, cleaved caspase-9 and PARP-1, increased with Pt(IV)(α-TOS)(OEt) treatment, revealing that cells underwent apoptosis. Therefore Pt(IV)(α-TOS)(OEt) induced DNA damage that resulted in apoptosis, like cisplatin and other Pt(IV)-based agents.

Figure 4C:
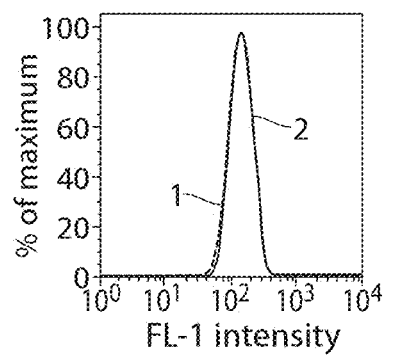
Figure 4C:
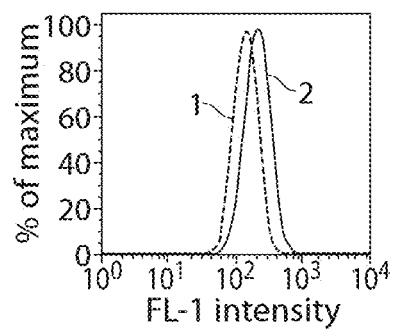
Figure 4B:
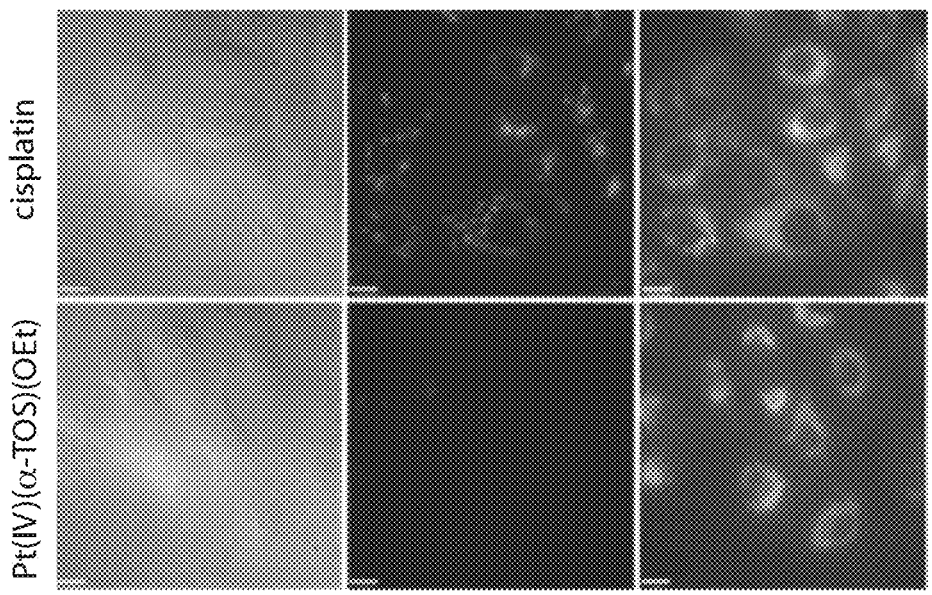
Figure 5:
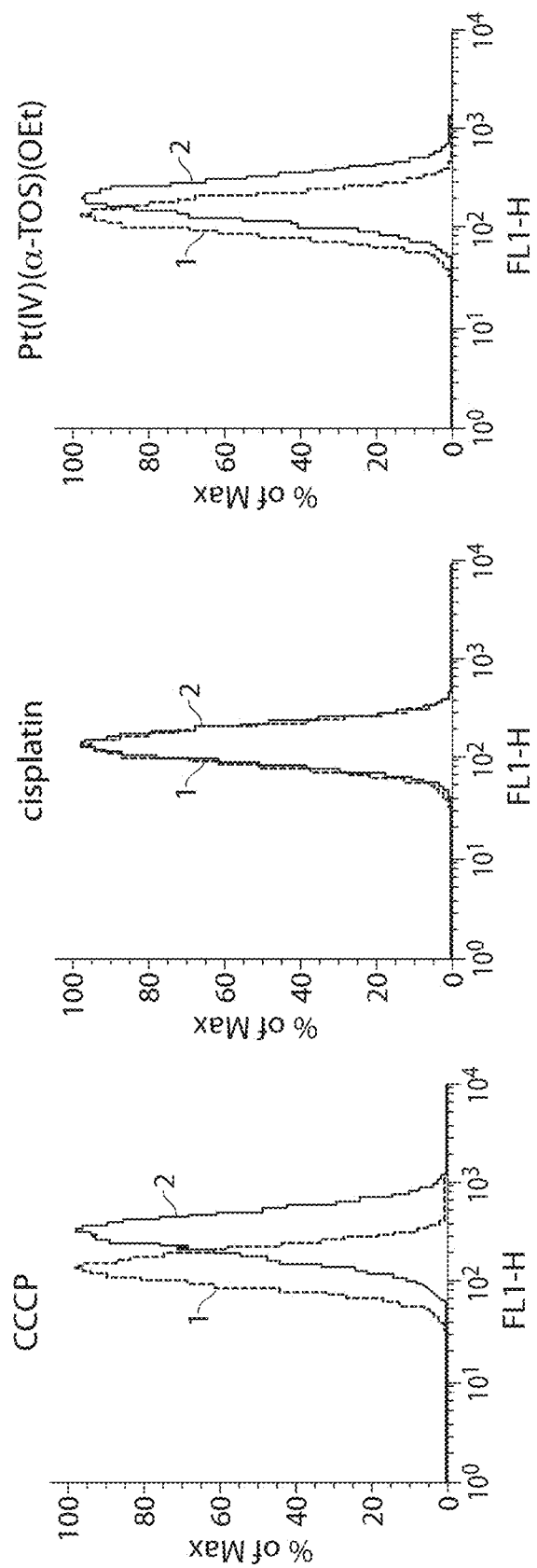
FIG. 5 shows histograms, produced from flow cytometry data of A549 cells treated with CCCP, representing the change in FL1-H for cells stained with JC-1 in absence (line 1) and presence (line 2) of CCCP, cisplatin, and Pt(IV)(α-TOS)(OEt)

To investigate the effect of Pt(IV)(α-TOS)(OEt) on mitochondria, changes in the mitochondrial membrane potential were assessed by the JC-1 assay. JC-1 (5,5',6,6'-tetrachloro-1,1'3,3'-tetraethylbenzimidazolylcarbocyanine iodide) is a positively charged lipophilic dye, which accumulates in the mitochondria of healthy cells as red-emitting aggregates. When the mitochondrial membrane is compromised, JC-1 de-aggregates into monomeric forms that emit green fluorescence. Untreated A549 cells showed both red and green fluorescence with slightly greater red fluorescence. Cells treated with mitochondrial membrane depolarizer, carbonyl cyanide m-chlorophenyl hydrazone (CCCP), had increased green fluorescence and diminished red fluorescence, indicative of mitochondrial membrane disruption. A similar phenomenon was observed in Pt(IV)(α-TOS)(OEt)—but not in cisplatin-treated cells, as shown in FIG. 4B. FIG. 4B shows fluorescence microscope images of A549 cells after a JC-1 assay in which the cells were treated with cisplatin or Pt(IV)(α-TOS)(OEt) at 20 µM, for 4 hours. These findings were confirmed using flow cytometry. A large population of untreated and Pt(IV)(α-TOS)(OEt)-treated A549 cells were examined. Upon Pt(IV)(α-TOS)(OEt) treatment, a marked increase in cells expressing green fluorescence was observed, indicative of unhealthy mitochondria as shown in FIGS. 4C and 5. FIG. 4C shows the histogram, produced from flow cytometry data from A549 cells treated with cisplatin or Pt(IV)(α-TOS)(OEt) at 25 µM, for 4 h, representing the change in FL1-H for cells stained with JC-1 in absence (line 1) and presence (line 2) of cisplatin (top) and Pt(IV)(α-TOS)(OEt) (bottom). FIG. 5 shows the histograms, produced from flow cytometry data from A549 cells treated with CCCP at 25 mM, cisplatin at 25 mM, and Pt(IV)(α-TOS)(OEt) at 25 mM, for 4 hours, representing the change in FL1-H for cells stained with JC-1 in absence (line 1 and presence (line 2) of CCCP, cisplatin, and Pt(IV)(α-TOS)(OEt). This observation demonstrated that Pt(IV)(α-TOS)(OEt) could cause disruption of mitochondrial function and promote apoptosis in cancer cells in an orthogonal manner to genomic DNA damage.

Figure 6:
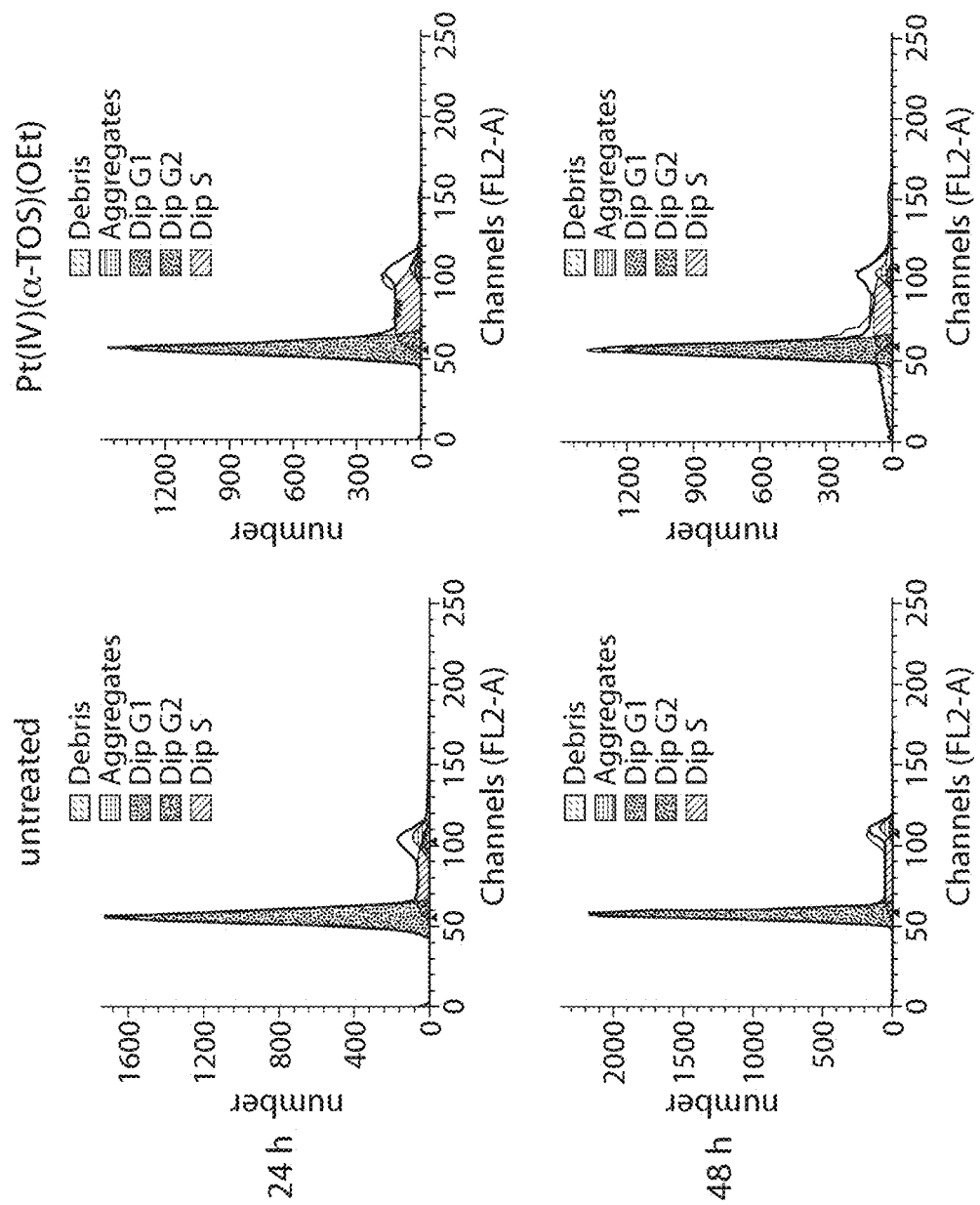
FIG. 6 shows histograms representing the different phases of the cell cycle for A549 cells in absence and presence of Pt(IV)(α-TOS)(OEt) over the course of 24 and 48 hours.

Flow-cytometric measurements were also performed to determine the effect of Pt(IV)(α-TOS)(OEt) exposure on cell cycle progression. A549 cells were treated with Pt(IV)(α-TOS)(OEt), 3 µM, for 24, and 48 hours. The cell cycle distribution was compared with untreated cells. FIG. 6 shows histograms representing the different phases of the cell cycle for A549 cells in absence and presence of Pt(IV)(α-TOS)(OEt) (3 µM) over the course of 48 h. After 24 hours the untreated population had 78.1% in G1 phase, 17.7% in S phase, 4.5% in G2/M phase. After 48 hours the untreated population had 81.0% in G1 phase, 16.0% in S phase, 3.0% in G2/M phase. After 24 hours the treated population had 64.7% in G1 phase, 31.7% in S phase, 3.6% in G2/M phase. After 48 hours, the treated population had 70.4% in G1 phase, 26.2% in S phase, 3.4% in G2/M phase. Thus, cells treated with Pt(IV)(α-TOS)(OEt) displayed large S-phase populations after 24 and 48 h, indicative of S-phase arrest. It was therefore clear that Pt(IV)(α-TOS)(OEt) disturbed DNA synthesis and arrest at S-phase.

Figure 7:
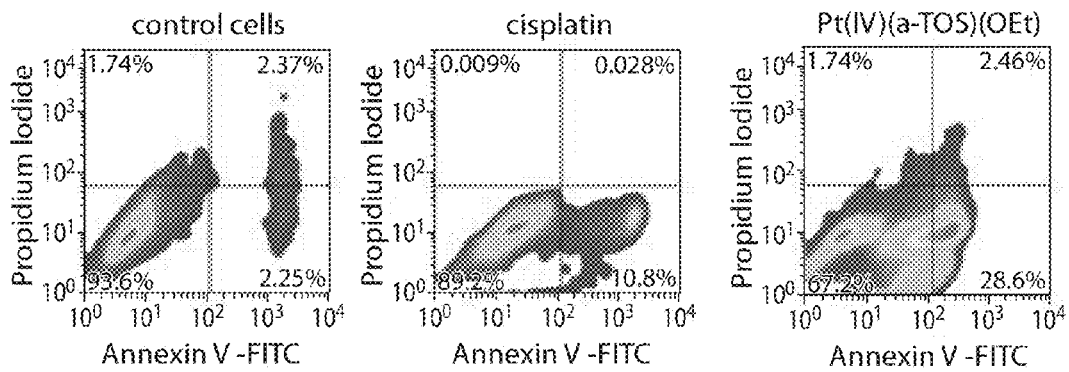
FIG. 7 shows FITC Annexin V/PI binding assay plots of untreated A2780 ovarian cancer cells (control) and A2780 ovarian cancer cells treated with Pt(IV)(α-TOS)(OEt) and cisplatin.

Finally, PI-annexin-V dual staining assay was performed to quantify apoptosis induced by Pt(IV)(α-TOS)(OEt) in A2780 ovarian cancer cells. After cells were exposed to Pt(IV)(α-TOS)(OEt) (4 μM) for 48 h, 28% of the cell population displayed characteristics associated with early apoptosis. Only 10% of cisplatin-treated cells displayed apoptotic properties; therefore, Pt(IV)(α-TOS)(OEt) showed a superior ability to induce apoptosis. The data are shown in FIG. 7. FIG. 7 shows FITC Annexin V/PI binding assay plots of untreated A2780 ovarian cancer cells (control), cells treated with Pt(IV) (α-TOS)(OEt) (4 μM for 48 hours), and cisplatin (10 μM for 48 hours).

In summary, the vitamin E analog α-TOS conjugated Pt(IV) compound, Pt(IV)(α-TOS)(OEt), displayed dual targeting effects in killing cancer cells. The platinum moiety caused nuclear DNA damage and α-TOS disrupted Bcl-xL-Bax interactions leading to mitochondrial dysfunction. Pt(IV)(α-TOS)(OEt) displayed superior efficacy in cell killing than cisplatin.

Example 4

This following example outlines the materials and methods used in Examples 1-3.

Materials and Methods.

Cisplatin was purchased from Strem Chemicals (Newburyport, Mass. USA). Unless otherwise noted, all chemicals were obtained from commercial sources and used as received. c,c,t-[PtCl$_2$(NH$_3$)$_2$(OH)$_2$] and α-TOS anhydride was synthesized was prepared according to a literature procedure.

Synthesis of Pt(IV)(α-TOS)$_2$.

α-TOS anhydride 2 g (1.94 mmol) and 162 mg (0.4850 mmol) of c,c,t-[PtCl$_2$(NH$_3$)$_2$(OH)$_2$] were mixed in 5 mL of DMF and stirred at 50° C. overnight. The resulting clear solution was filtered through Celite. A 200 mL portion of water was added to the filtrate, which was subsequently extracted with 100 mL of ethyl acetate. The aqueous phase was further extracted with 100 mL of diethyl ether. The diethyl ether and ethyl acetate portions were combined and dried over Na$_2$SO$_4$. After removal of the solvent under vacuum, 50 mL of methanol was added and the solution was cooled to −20° C. A yellowish-white precipitate formed and was collected by centrifugation. The solid was dried under vacuum to yield 390 mg, 60%. $^1$H NMR (500 MHz, CDCl$_3$), δ (ppm) 5.61, (b, 3H), 2.92 (t, 2H), 2.69 (t, 2H), 2.57 (t, 2H), 2.08 (s, 3H), 1.99 (s, 3H), 1.95 (s, 3H), 1.76 (m, 2H), 1.53-1.09 (m, 30H), 0.86 (m, 12H); $^{13}$C NMR (125 MHz, CDCl$_3$): 6 (ppm) 183.2, 173.9, 150.3, 141.0, 127.3, 125.7, 123.8, 118.2, 75.9, 40.1, 38.2, 38.0, 33.5, 33.4, 32.0, 30.8, 28.7, 25.5, 25.2, 23.4, 23.3, 21.7, 21.3, 20.5, 20.3, 13.9, 13.0, 12.6. $^{195}$Pt{$^1$H}c NMR (86 MHz, CDCl$_3$) δ (ppm) 1048.5. ESI-MS: m/z Calcd [M−H]$^−$ 1357.7. Found 1357.8. Anal. Calcd for C$_{66}$H$_{112}$Cl$_2$N$_2$O$_{10}$Pt. C, 58.30; H, 8.30; N, 2.06. Found: C, 57.98; H, 7.91; N, 1.92.

Synthesis of Pt(IV)(α-TOS)(OEt).

α-TOS anhydride 200 mg (0.194 mmol) and 30 mg (0.082 mmol) of c,c,t-[PtCl$_2$(NH$_3$)$_2$(OH)(OEt)] were mixed in 5 mL of DMF/EA (1:4 v/v) and stirred at 50° C. overnight. The resulting clear solution was filtered through Celite. The solvent was removed under vacuum and the crude product was purified by column chromatography using EA/MeOH (10%) as an eluent. The final product is a yellowish-white solid, yield 81 mg, 42%. $^1$H NMR (500 MHz, CDCl$_3$), δ (ppm) 5.2, (br, 5H), 2.3 (t, 2H), 2.9 (t, 2H), 2.7 (t, 2H), 2.6 (t, 2H), 2.08 (s, 3H), 2.0-2.1 (2 s, 12H), 1.9 (m, 3H), 1.53-1.09 (m, 34H), 0.86 (m, 15H); $^{13}$C NMR (100 MHz, CDCl$_3$): δ (ppm) 181.8, 173.6, 149.7, 141.1, 127.2, 125.7, 123.0, 118.0, 75.4, 67.6, 37.7, 29.0, 28.5, 25.2, 24.8, 22.5, 22.4, 20.9, 19.6, 16.7, 12.7, 11.8, 11.4. $^{195}$Pt{$^1$H}NMR (86 MHz, CDCl$_3$) δ (ppm) 879.9. ESI-MS: m/z Calcd [M−H]$^−$ 873.8. Found 873.4. Anal. Calcd for (M+H$_2$O)C$_{35}$H$_{66}$Cl$_2$N$_2$O$_7$Pt. Calcd. C, 47.08; H, 7.45; N, 3.14. Found C, 47.11; H, 6.97; N, 3.03.

Instrumentation.

NMR data were recorded on a Bruker DPX-400 or VARIAN Inova-500 spectrometer in the MIT Department of Chemistry Instrumentation Facility (DCIF). $^1$H and $^{13}$C NMR spectra were referenced internally to residual solvent peaks, and chemical shifts are expressed relative to tetramethylsilane (δ=0 ppm). $^{195}$Pt NMR spectra were referenced externally using a standard of K$_2$PtCl$_4$ in D$_2$O (δ=−1628 ppm). Electrospray ionization mass spectrometry (ESI-MS) measurements were acquired on an Agilent Technologies 1100 series LC-MSD trap. Graphite furnace atomic absorption spectrometry was carried out using a Perkin-Elmer AAnalyst600 GF-AAS.

Cell Lines and Culture Conditions.

(a) Dulbecco's Modified Eagle Medium (DMEM), Dulbecco's phosphate buffered saline (DPBS), fetal bovine serum (FBS) and 0.25% trypsin/EDTA solutions were purchased from Cellgro (Manassas, Va.). Penicillin-streptomycin solutions were purchased from Mediatech (Manassas, Va.). (b) HeLa (CCL-2TM) cells, A549, A2870, A2870/CP70, MCF-7, PC-3, and MRC-5 cells were purchased from American Type Culture Collection (ATCC, Manassas, Va., USA). (c) HCT116 cells were kindly donated by Laura Trudel (MIT). HeLa, A549, MCF-7, and MRC-5 cells were cultured using DMEM supplemented with 10% FBS and 1% penicillin-streptomycin. A2870, A2870/CP70, and PC-3 cells were cultured in RPMI supplemented with 10% FBS and 1% penicillin-streptomycin. HCT116 cells were cultured in McCoy's supplemented with 10% FBS and 1% penicillin-streptomycin. All cell-culture experiments were performed in the aforementioned media in an incubator operating at 37° C. and in the presence of a humidified atmosphere containing 5.0% CO$_2$. Cells were harvested using a 0.25% trypsin/EDTA solution.

Cytotoxicity Tests in Cancer Cell Lines.

The cytotoxicity of the compounds was assessed by means of the MTT assay (MTT=3-(4,5-dimethyl-2-thiazolyl)-2,5-diphenyl-2H-tetrazolium bromide). Typically, on day one, ~1×10$^3$ cells were seeded into 96-well plates in 100 μL media per well. The last row of the plate was left empty as a control for background absorption. The cells were allowed to grow for 24 h in the incubator at 37° C. On day two, a series of drug dilutions in growth media were prepared immediately prior to cell treatment. The media in the wells of the 96 plates were replaced with 100 μL of growth media containing appropriate drug concentrations. The cells were treated for 48 h at 37° C. in the incubator. On day four, a stock solution of MTT (5 mg/mL in PBS buffer) was diluted with media so that, when 100 μL of the media was added to each well, 10 μL of MTT stock was applied. The cells were incubated for 2 h and then all the media was replaced with 100 μL of DMSO to dissolve the purple MTT-formazan crystals. The optical density for each well at 550 nm was measured with a microplate reader.

Cellular Uptake.

To measure the cellular uptake of the platinum complexes, ca. 1 million A549 cells were treated with 10 μM of the complexes at 37° C. for 3 h. Then the media was removed, the cells were washed with PBS solution (1 mL×3), harvested, and centrifuged. The cellular pellet was suspended in an appropriate volume of PBS to obtain a homogeneous cell suspension (eg. 100 µL). The suspension was divided in two. One part was used to analyze the metal content in the whole cell and the other was used for analysis of the cytoplasmic and nucleus. The Thermo Scientific NE-PER Nuclear and Cytoplasmic Extraction Kit was used to extract the separate cytoplasmic, nuclear, and membrane fractions. The remaining cell suspension was mineralized with 65% $HNO_3$ and then completely dried at 120° C. The solid extracts were re-dissolved in 2% $HNO_3$ and analysed using GF-AAS. Cellular platinum levels were expressed as pmol Pt per million cells. Results are presented as the mean of 3 determinations for each data point.

Intracellular DNA Platinum Content.

To measure the amount platinum on genomic DNA, ca. 1 million A549 cells were treated with 10 µM of the test compounds at 37° C. for 3 h. The nucleus was extracted using the Thermo Scientific NE-PER Nuclear and Cytoplasmic Extraction Kit. The nuclear pellet was suspended in DNAzol (1 mL, genomic DNA isolation reagent, MRC). The genomic DNA was precipitated with ethanol (0.5 mL), washed with 75% ethanol (0.75 mL×3), and re-dissolved in 200 µL of 8 mM NaOH. The DNA concentration was determined by UV-visible spectroscopy, and platinum, was quantified by GFAAS. The reported values are the average of at least three independent experiments with the error reported as the standard deviation.

Flow Cytometry.

In order to monitor the cell cycle, flow cytometry studies were carried out. A549 cells were incubated with and without the test compounds for 24 and 48 h at 37° C. Cells were harvested from adherent cultures by trypsinization and combined with all detached cells from the incubation medium to assess total cell viability. Following centrifugation at 1000 rpm for 5 min, cells were washed with PBS and then fixed with 70% ethanol in PBS. Fixed cells were collected by centrifugation at 2500 rpm for 3 min, washed with PBS and centrifuged as before. Cellular pellets were re-suspended in 50 µg/mL propidium iodide (Sigma) in PBS for nucleic acids staining and treated with 100 µg/mL RNaseA (Sigma). DNA content was measured on a FACSCalibur-HTS flow cytometer (BD Biosciences) using laser excitation at 488 nm and 20,000 events per sample were acquired. Cell cycle profiles were analysed using the ModFit software. For the apoptosis experiments, the Annexin V-FITC Early Apoptosis Detection Kit (Cell Signaling Technology) was used. The manufacture's protocol was followed to carry out this experiment. Briefly, untreated and treated cells ($1\times10^5$) were suspended in 1× annexin binding buffer (96 µL) (10 mM HEPES, 140 mM NaCl, 2.5 mM $CaCl_2$, pH 7.4), then 1 µL FITC annexin V and 12.5 µL propidium iodine (10 µg/mL) were added to each sample and incubated on ice for 15 min. Subsequently, more binding buffer (150 µL) was added while gently mixing. The samples were kept on ice prior to being read on the FACSCalibur-HTS flow cytometer (BD Biosciences) (20,000 events per sample were acquired). Cell populations were analysed using the FlowJo software (Tree Star). For the JC-1 assay, the JC-1 Mitochondrial Membrane Potential Assay Kit (Cayman) was used. The manufacture's protocol was followed to carry out this experiment. Briefly, to untreated and treated cells grown in 6-well plates (at a density of $5\times10^5$ cells/mL) was added the JC-1 staining solution (100 µL/mL of cell media). The cells were incubated for 30 min, harvested, and analysed by using the FACSCalibur-HTS flow cytometer (BD Biosciences) (20,000 events per sample were acquired). The FL1 channel was used to detect unhealthy or apoptotic cells with collapsed mitochondria. Cell populations were analysed using the FlowJo software (Tree Star).

Immunoblotting Analysis.

A549 cells ($5\times10^5$ cells) were incubated with test compound for 48 h at 37° C. Cells were washed with PBS, scraped into SDS-PAGE loading buffer (64 mM Tris-HCl (pH6.8)/ 9.6% glycerol/2% SDS/5% β-mercaptoethanol/0.01% Bromophenol Blue) and incubated at 95° C. for 10 min. Whole cell lysates were resolved by 4-20% sodium dodecylsulphate polyacylamide gel electrophoresis (SDS-PAGE; 200 V for 1 h) followed by electro transfer to polyvinylidene difluoride membrane, PVDF (350 mA for 1 h). Membranes were blocked in 5% (w/v) non-fat milk in PBST (PBS/0.1% Tween 20) and incubated with the appropriate primary antibodies (Cell Signalling Technology and Santa Cruz). After incubation with horseradish peroxidase-conjugated secondary antibodies (Cell Signalling Technology), immune complexes were detected with the ECL detection reagent (BioRad) and analysed using an Alpha Innotech ChemiImager™ 5500 fitted with a chemiluminescence filter.

Co-Immunoprecipitation.

A549 cells ($5\times10^5$ cells) were incubated with test compound for 48 h at 37° C. Cells were washed with PBS, scraped into RIPA buffer (250 µL, 50 mM Tris-HCl, pH 7.4, 1% Nonidet P-40, 0.25% sodium deoxycholate, 150 mM NaCl, 1 mM EDTA, and 1% protease inhibitor mixture) and gently mixed for 15 min. The resultant cell lysate was treated with protein A-agarose bead slurry (50 µL) and centrifuged to remove proteins that bind non-specifically. Anti Bcl-XL antibody (Cell Signalling Technology) was added to the lysate and incubated for 2 h at room temperature. Protein A-agarose bead slurry (50 µL) was added and the mixture was incubated at 4° C. overnight. Centrifugation allowed separation of the immunocomplex, which was washed with cold RIPA buffer (3×500 µL). The immunocomplex was then suspended in SDS-PAGE loading buffer (50 µL) and incubated at 95° C. for 10 min. The solution containing the immunocomplex was isolated by centrifugation and then analysed for Bax content using the immunoblotting analysis protocol described above.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A platinum(IV) compound comprising at least one vitamin E analog, wherein the vitamin E analog is associated with the platinum center and wherein the vitamin E analog is tocotrienol or a tocotrienol analog.

2. A platinum(IV) compound comprising at least one vitamin E analog, wherein the vitamin E analog is associated with the platinum center and wherein the vitamin E analog is of the formula:

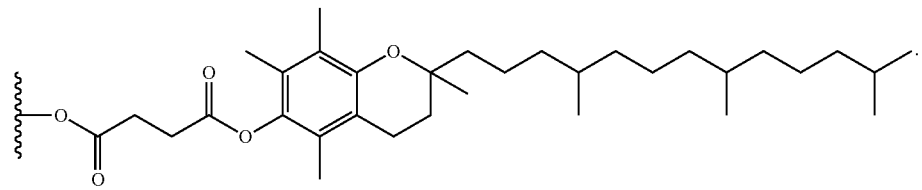 [SMILES: *OC(=O)CCC(=O)Oc1c(C)c(C)c2c(c1C)CCC(C)(CCCC(C)CCCC(C)CCCC(C)C)O2]

3. A platinum(IV) compound comprising at least one vitamin E analog, wherein the vitamin E analog is associated with the platinum center and wherein the vitamin E analog is of the formula:

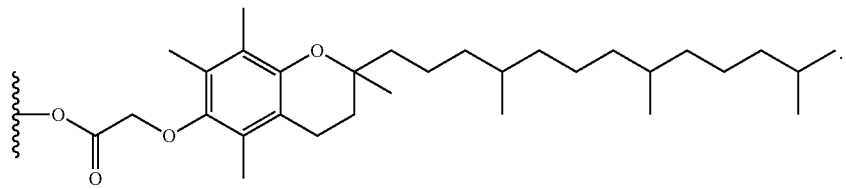 [SMILES: *OC(=O)COc1c(C)c(C)c2c(c1C)CCC(C)(CCCC(C)CCCC(C)CCCC(C)C)O2]

4. A platinum(IV) compound comprising at least one vitamin E analog, wherein the vitamin E analog is associated with the platinum center and wherein the vitamin E analog is of the formula:

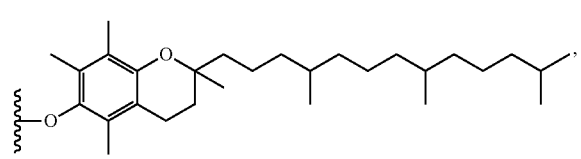 [SMILES: *Oc1c(C)c(C)c2c(c1C)CCC(C)(CCCC(C)CCCC(C)CCCC(C)C)O2]

5. A platinum(IV) compound comprising at least one vitamin E analog, wherein the vitamin E analog is associated with the platinum center and wherein the vitamin E analog dissociates from the platinum center upon reduction of the platinum center.

6. A platinum(IV) compound comprising at least one vitamin E analog, wherein the vitamin E analog is associated with the platinum center and wherein the compound has the formula:

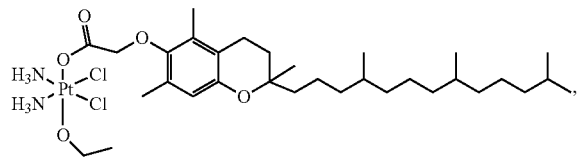

,

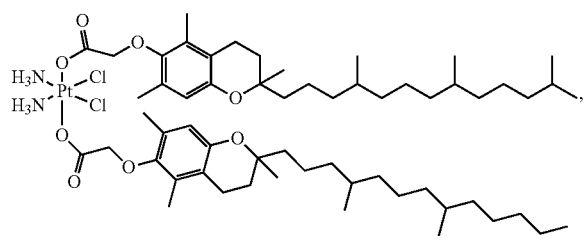

,

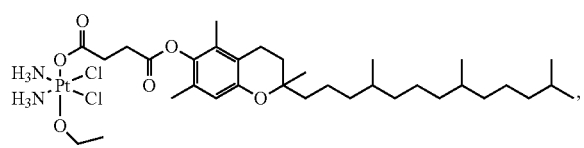

, or

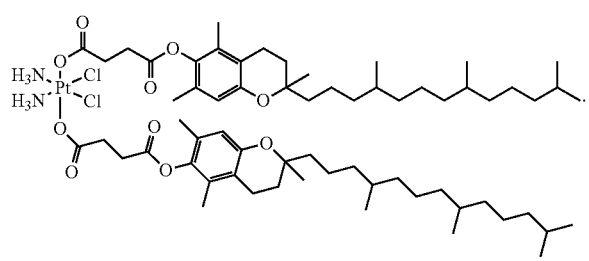

.

7. A pharmaceutical composition, comprising:
a platinum(IV) compound as in claim 6, or a pharmaceutically acceptable salt, thereof; and
one or more pharmaceutically acceptable carriers, additives and/or diluents.

8. A method of treating cancer in a patient in need of treatment for cancer, comprising:
administering to the patient a platinum(IV) compound comprising at least one vitamin E analog, wherein the vitamin E analog is associated with the platinum center,
wherein, upon uptake of the composition into a cell, the platinum(IV) compound dissociates to form a therapeutically active platinum(II) compound and the vitamin E analog, and
wherein the cancer is lung cancer, cervical cancer, or ovarian cancer.

9. The method of claim 8, wherein the cancer is cisplatin-resistant ovarian cancer.

10. A pharmaceutical composition, comprising:
a platinum(IV) compound as in claim 1, or a pharmaceutically acceptable salt, thereof; and
one or more pharmaceutically acceptable carriers, additives and/or diluents.

11. A pharmaceutical composition, comprising:
a platinum(IV) compound as in claim 2, or a pharmaceutically acceptable salt, thereof; and
one or more pharmaceutically acceptable carriers, additives and/or diluents.

12. A pharmaceutical composition, comprising:
a platinum(IV) compound as in claim 3, or a pharmaceutically acceptable salt, thereof; and
one or more pharmaceutically acceptable carriers, additives and/or diluents.

13. A pharmaceutical composition, comprising:
a platinum(IV) compound as in claim 4, or a pharmaceutically acceptable salt, thereof; and
one or more pharmaceutically acceptable carriers, additives and/or diluents.

14. A pharmaceutical composition, comprising:
a platinum(IV) compound as in claim 5, or a pharmaceutically acceptable salt, thereof; and
one or more pharmaceutically acceptable carriers, additives and/or diluents.

15. The platinum(IV) compound of claim 3, wherein the compound has the formula:

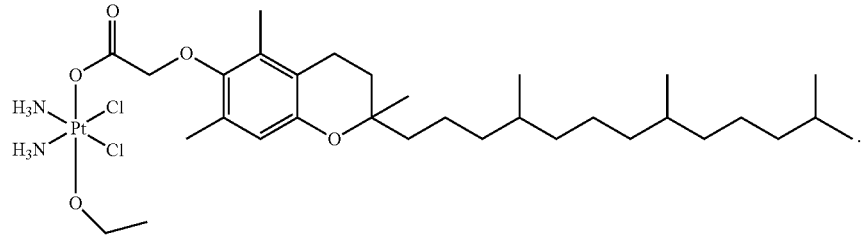

.

16. The platinum(IV) compound of claim 3, wherein the compound has the formula:
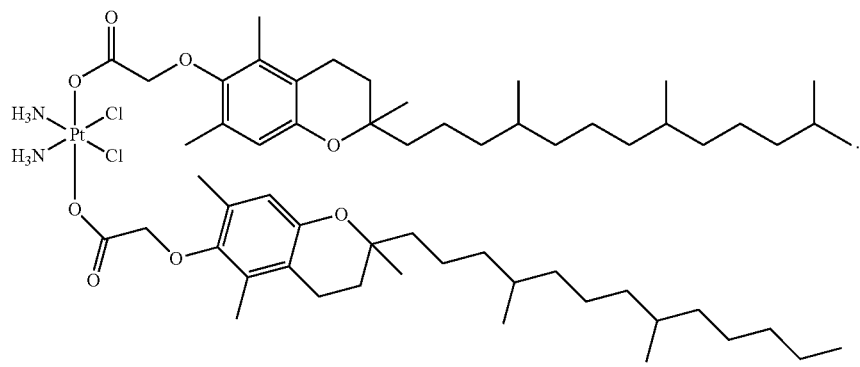
17. The platinum(IV) compound of claim 2, wherein the compound has the formula:
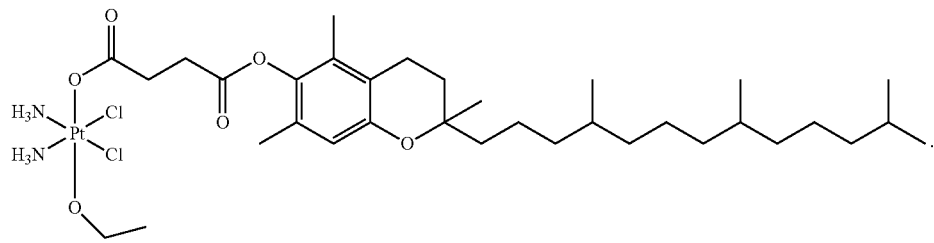
18. The platinum(IV) compound of claim 2, wherein the compound has the formula:
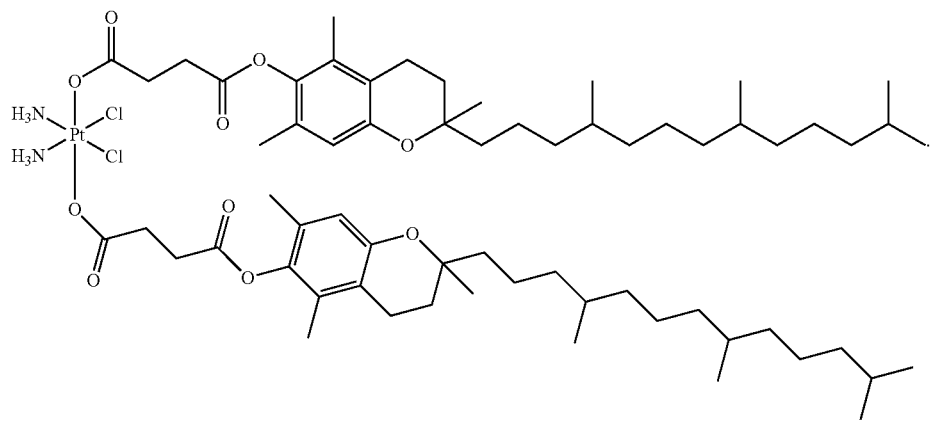
* * * * *